(12) United States Patent
Yajima et al.

(10) Patent No.: US 8,575,569 B2
(45) Date of Patent: Nov. 5, 2013

(54) FLUORESCENCE IMAGING APPARATUS AND METHOD FOR DETECTING FLUORESCENT IMAGE

(75) Inventors: Atsushi Yajima, Kizugawa (JP); Ichiro Oda, Uji (JP); Kentaro Hizume, Kyoto (JP); Yoshio Tsunazawa, Joyo (JP)

(73) Assignee: Shimadzu Corporation, Kyoto-Shi (JP)

( * ) Notice: Subject to any disclaimer, the term of this patent is extended or adjusted under 35 U.S.C. 154(b) by 93 days.

(21) Appl. No.: 13/119,418

(22) PCT Filed: Sep. 18, 2008

(86) PCT No.: PCT/JP2008/066865
§ 371 (c)(1),
(2), (4) Date: Mar. 16, 2011

(87) PCT Pub. No.: WO2010/032306
PCT Pub. Date: Mar. 25, 2010

(65) Prior Publication Data
US 2011/0168915 A1    Jul. 14, 2011

(51) Int. Cl.
G01J 1/58    (2006.01)
H01J 40/14    (2006.01)

(52) U.S. Cl.
USPC ............... 250/458.1; 250/226; 250/459.1

(58) Field of Classification Search
USPC ................. 250/459.1, 226, 458.1
See application file for complete search history.

(56) References Cited

U.S. PATENT DOCUMENTS

| | | | |
|---|---|---|---|
| 4,573,195 A | 2/1986 | de France | |
| 5,214,494 A | 5/1993 | Inaba et al. | |
| 5,534,703 A | 7/1996 | Kambara et al. | 250/458.1 |
| 6,351,663 B1* | 2/2002 | Flower et al. | 600/476 |
| 7,453,568 B2 | 11/2008 | Kawamata et al. | |
| 2005/0018332 A1 | 1/2005 | Vizard et al. | |
| 2005/0029437 A1 | 2/2005 | Hasegawa et al. | 250/226 |
| 2005/0231715 A1 | 10/2005 | Horigome et al. | |

FOREIGN PATENT DOCUMENTS

| | | | |
|---|---|---|---|
| CN | 1777802 A | | 5/2006 |
| CN | 1287735 C | | 12/2006 |
| DE | 3920043 A1 | | 1/1991 |
| EP | 1067376 A2 | | 1/2001 |
| EP | 1757923 A2 | | 2/2007 |
| JP | 06-294739 | | 10/1994 |
| JP | 2002-267934 | | 9/2002 |
| JP | 2005-087728 | | 4/2005 |
| JP | 2005-152130 | | 6/2005 |

OTHER PUBLICATIONS

Chinese language office action dated Jul. 17, 2012 issued in corresponding Chinese application 200880131183.3.
Supplementary European Search Report issued Feb. 22, 2013 for European Application No. EP08810908, 10 pages.

(Continued)

*Primary Examiner* — David Porta
*Assistant Examiner* — Kenneth J Malkowski
(74) *Attorney, Agent, or Firm* — Bingham McCutchen LLP

(57) ABSTRACT

In order to reduce light leak influencing the detection capability of a fluorescence imaging apparatus, an interference filter and an absorption filter on an emission-side filter section are arranged serially in the traveling direction of the fluorescence. The interference filter and the absorption filter that are in use for such an arrangement block the waveband light equivalent to the excitation light irradiated onto a sample while fully transmitting the waveband light equivalent to the fluorescence.

12 Claims, 20 Drawing Sheets

(56) References Cited

OTHER PUBLICATIONS

Chinese Office Action dated May 22, 2013 for the realted Chinese Patent App. No. 2008801311833.

English Translation of the "Second Notification of Reason for Rejection" of Chinese Office Action dated May 22, 2013 for Chinese App. No. 2008801311833.

* cited by examiner

PRIOR ART

PRIOR ART

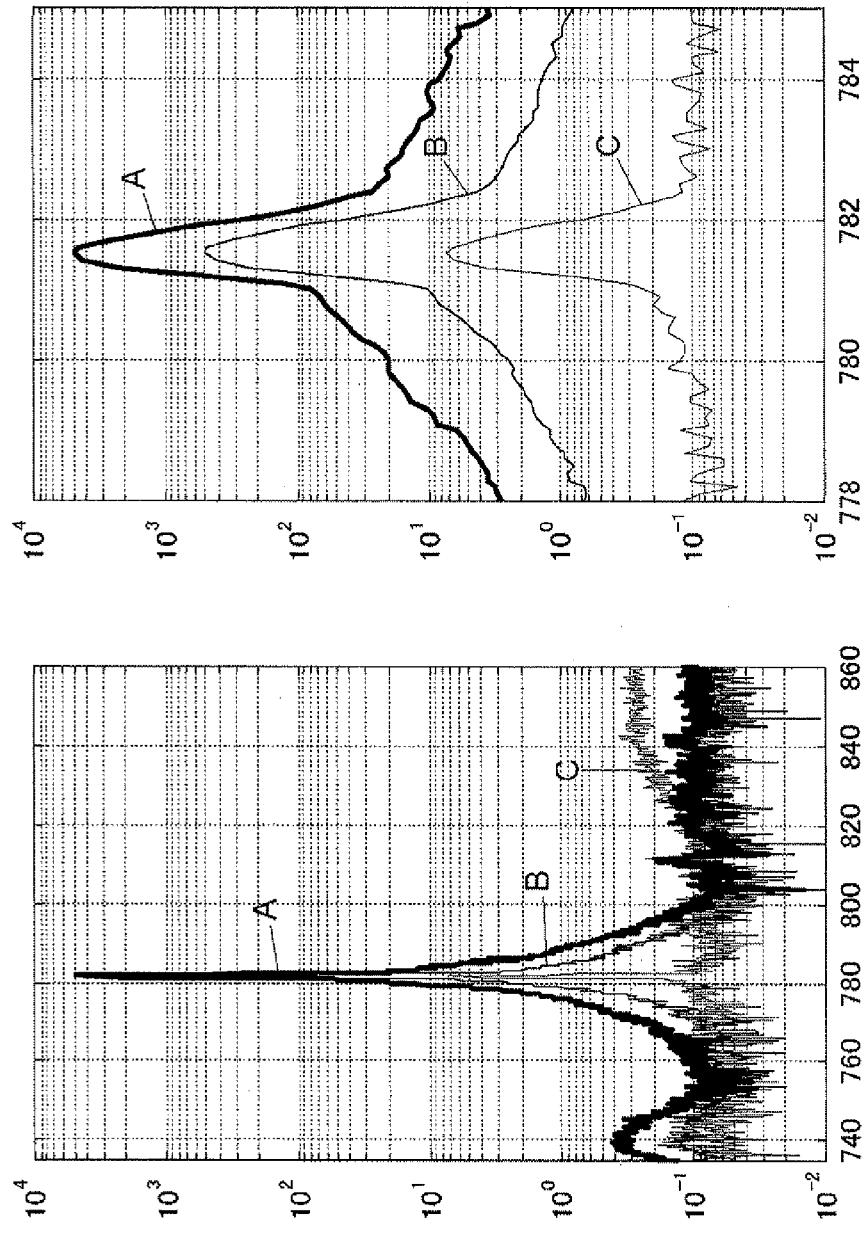

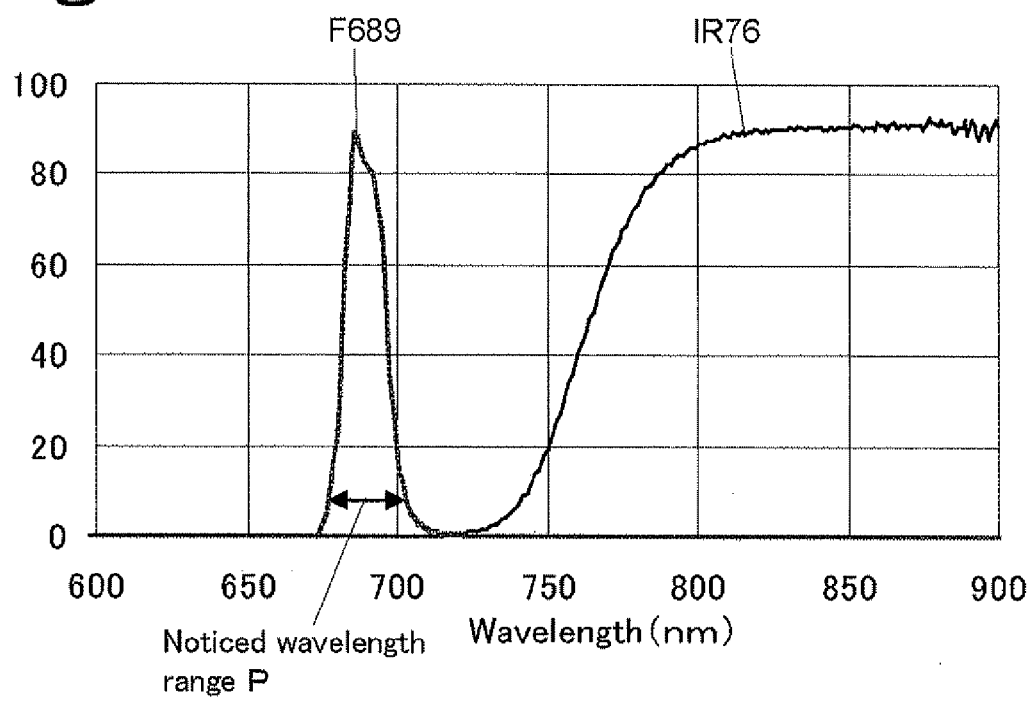

FLUORESCENCE IMAGING APPARATUS AND METHOD FOR DETECTING FLUORESCENT IMAGE

CROSS-REFERENCE TO THE RELATED APPLICATIONS

This application is a national stage of international application No. PCT/JP2008/066865 filed on Sep. 18, 2008, the entire contents of which are incorporated herein by reference.

BACKGROUND OF THE INVENTION

1. Field of the Invention

The present invention relates to an optical bio-imaging technique using fluorescence detection.

2. Description of the Related Art

The method for attaining imaging as to what state a molecular species in a living body or in cells is distributed into is an important researching method in medical science or biology. At the level of cells, the following method has widely been performed: a method of using a microscope to image a molecular species with a molecular probe to which a fluorescent dye adheres or a gene-expression molecular probe. Regarding those which are larger than cells, such as internal organs, and further, animal individuals, a device has been required for observing considerable molecular species and the state of their distribution while alive.

The method is, for example, a technique of bonding a fluorescent probe to a cancer cell in an individual of a mouse or some other, imaging the situation of the proliferation of the cancer cell, to which attention is paid, and observing the situation every day or every week to analyze a change in the situation with the passage of time. In order to watch the proliferation of cancer cells inside an individual of an animal by means of a conventional cell-level-observing measuring device, the animal is killed and then a predetermined region thereof is dyed or a fluorescent substance is attached thereto so as to observe the region. However, according to the method, it is impossible to watch the proliferation of cells of a single individual with the passage of time over a long term. For this reason, it has been desired to develop a device capable of observing a molecular species of an individual of a small animal, as internal information thereof, in the state that the individual is alive.

FIG. 10 is a view illustrating an example of a typical fluorescence imaging apparatus.

According to this device, out of light rays from a light source 16, light rays having wavelengths selected through an excitation-side filter 11 ($F_{ex}$) are radiated, as excitation light, onto a living sample, and then fluorescent components of scattered light rays therefrom are taken out through an emission-side filter 12 ($F_{em}$) so as to form an image on a CCD camera 38, which is a two-dimensional detecting unit, through an imaging lens 32. In this way, a fluorescent image of the sample is obtained.

In such a device, at the time of radiating excitation light onto a sample, its fluorescent molecule to which attention is paid emits light having a wavelength different from that of the excitation light, normally, light having a wavelength longer than that of the excitation light; thus, when a filter which blocks the wavelength components of the excitation light completely is set up as the emission-side filter 12 between the sample and the two-dimensional detecting unit 38, only the fluorescent wavelength components can be detected with a good sensitivity.

Actually, however, the spectrum of the excitation light radiated onto the sample slightly contains therein light having the same wavelengths as the fluorescent components (the light may also be referred to as stray light) in many cases. The stray light is reflected on the sample, and overlapped with the fluorescence emitted from the sample so as to deteriorate the detection limit of the fluorescence. If the excitation light radiated onto the sample does not contain stray light at all, the following drawback is caused when the emission-side filter is insufficient in capability so as not to remove the wavelength components of the excitation light completely: components of the excitation light reflected on the sample are partially transmitted through the emission-side filter so as to overlap with the fluorescent components from the sample, so that the detection limit of the fluorescence is deteriorated. The deterioration in the fluorescence detection limit causes feeble fluorescent components to be buried in noises, so that the fluorescent components cannot be vividly imaged. In a case where at the time of causing a fluorescent dye to adhere onto a notable region of a living sample and observing the region the notable region is present around a central position of the living sample, that is, around a position farther from the surface thereof, the intensity of the fluorescence captured from the surface of the living sample becomes weak accordingly. When the fluorescence detection limit is bad, such feeble fluorescent components cannot be vividly captured.

SUMMARY OF THE INVENTION

Thus, an object of the present invention is to provide a fluorescence imaging apparatus making it possible to improve the detection limit of fluorescence to detect even a feeble fluorescence with a good sensitivity.

FIG. 11 is a chart showing an excitation spectrum 45 and a fluorescence spectrum 46 of a fluorescent dye contained in a sample in a fluorescence imaging apparatus as shown in FIG. 10; and a transmission property 41 of an excitation-side filter 11 ($F_{ex}$) and a transmission property 42 of an emission-side filter 12 ($F_{em}$), the filters 11 and 12 being selected correspondingly to the spectra 45 and 46. The transmission wavelength band of the excitation-side filter 11 is selected to be contained in the wavelength range in which the excitation spectrum 45 shows a large intensity. The fluorescence spectrum 46 is shifted to longer wavelengths than those of the excitation spectrum 45; thus, correspondingly thereto, the transmission property 42 of the emission-side filter 12 is selected so as to also be shifted to longer wavelengths than those of the excitation-side filter 11.

FIG. 12 is a graph showing a specific example of the transmission properties of the excitation-side filter $F_{ex}$ and the emission-side filter $F_{em}$. In this graph, wavelength (nm) and transmittance (the logarithm thereof) are taken on the transverse axis and the vertical axis, respectively. Regarding the transmittance on the vertical axis, one (represented as 1.E+00) is the maximum, so as to mean a transmittance of 100%. Usually, filters used as the excitation-side filter $F_{ex}$ and the emission-side filter $F_{em}$ are each a multi-layered interferece filter. The multi-layered interferece filter is a filter having a multilayered film structure wherein dielectric thin films of two kinds different from each other in refractive index are alternately stacked up into several tens of layers on a transparent support, whereby only light having desired wavelengths is transmitted and light having the other wavelengths is blocked (reflected).

In FIG. 12, the excitation-side filter $F_{ex}$ is a bandpass filter having a transmission wavelength band in the range of 630 to 690 nm (the width of the transmission wavelength band:

$\Delta\lambda_{ex}$). Further, regarding this excitation-side filter $F_{ex}$, if we focus on transmittance of the transmission wavelength band alone, it has a sufficiently high value of roughly 90%; which is not an issue. However, a transmittance of about $2\times10^{-6}$ ("$\times10^{-6}$" is represented as E-06) exists even in a wavelength band at which light should be blocked. Thus, leak light exists in a wavelength band other than the transmission wavelength band. The leak transmittance of the excitation-side filter $F_{ex}$ is represented by "$t_{ex}$".

Meanwhile, the emission-side filter $F_{em}$ is a bandpass filter having a transmission wavelength band in the range of 730 to 780 nm (the width of the transmission wavelength band: $\Delta\lambda_{em}$). Further, regarding this emission-side filter $F_{em}$ also, if we focus on transmittance of the transmission wavelength band alone, it has a sufficiently high value of roughly 90%; which is not an issue. However, a transmittance of about $1\times10^{-5}$ exists even in a wavelength band at which light should be blocked. Thus, leak light exists in a wavelength band other than the transmission wavelength band. The leak transmittance of the emission-side filter $F_{em}$ is represented by "$t_{em}$".

In the example in FIG. 10, using the filter $F_{ex}$ (the transmission property: 41) and the filter $F_{em}$ (the transmission property: 42) in FIG. 12 and further using a continuous spectrum light source, such as a tungsten iodide lamp, consideration is taken with reference to FIGS. 13(a) to (c).

As shown in FIG. 13(a), it is presupposed that the intensity of light from a light source 16 is even over all wavelengths, and I (mW/nm). When the transmittance of the $F_{ex}$ in the transmission wavelength band thereof is regarded as 1 (100%) for simplification, the intensity of excitation light transmitted through the transmission wavelength band of the excitation-side filter $F_{ex}$ corresponds to an area in the figure. Thus, the intensity is:

$$I*\Delta\lambda_{ex}(mW).$$

When it is presupposed that a sample is a white scattering body which scatters excitation light as it is without emitting any fluorescence at all, the intensity of the scattered light traveling toward the excitation-side filter $F_{em}$ is:

$$I*\Delta\lambda_{ex}*k$$

wherein k is the ratio of the scattered light traveling toward the emission-side filter $F_{em}$. When the ratio of the leak light to the scattered light radiated into the emission-side filter $F_{em}$ is defined as the total leak factor (LF), the intensity of the leak light reaching the two-dimensional detecting unit 38 is:

$$I*\Delta\lambda_{ex}*k*LF.$$

It has been presupposed that no fluorescence is emitted from the sample; thus, when LF is 0, the CCD camera 38 takes a photograph of a pitch-black image. Since k is constant, the estimation of LF is equal to the estimation of the percentage of leak light contained in the transmitted light from the emission-side filter 12 in the state that as illustrated in FIG. 13(b), the excitation-side filter 11 and the emission-side filter 12 are arranged in series in the traveling direction of light from the light source 16. In short, it is sufficient for the consideration thereof that k is regarded as 1.

When the spectrum of the leak light from the emission-side filter 12 is measured in the arrangement in FIG. 13(b), two wavelength-component peaks $S_{ex}$ and $S_{em}$ as illustrated in FIG. 13(c) are detected. The left-side component $S_{ex}$ in the figure is a component resulting from a matter that light having wavelengths corresponding to the excitation light is not completely blocked because of a shortage in the capability of the emission-side filter 12. When the leak factor $t_{em}$ of the emission-side filter 12 is used, the following equation is obtained:

$$S_{ex}=I*\Delta\lambda_{ex}*t_{em}$$

It can be mentioned that the right-side component $S_{em}$ in the figure is a component resulting from a matter that because of a shortage in the capability of the excitation-side filter 11 (the leak factor=$t_{ex}$), leak light having an intensity of $I*t_{ex}$ reaches the emission-side filter 12, and out of rays of the light, light rays having wavelengths in the transmission wavelength band $\Delta\lambda_{em}$ of the emission-side filter 12 are transmitted, as they are, through the emission-side filter 12 (since the transmittance in the transmission wavelength band is regarded as 1). Accordingly, the following equation is obtained:

$$S_{em}=I*\Delta\lambda_{em}*t_{ex}$$

The intensity of the final leak light, which is radiated unfavorably into the two-dimensional detecting unit 38, is the sum of $S_{ex}$ at the excitation wavelengths and $S_{em}$ at the fluorescence-detected wavelengths. Accordingly, as the total leak factor LF is the ratio of the leak light to the scattered light radiated into the emission-side filter $F_{em}$, the factor LF can be defined as follows:

$$LF=(S_{em}+S_{ex})/(I*\Delta\lambda_{ex})$$
$$=(t_{em}*\Delta\lambda_{ex}+t_{ex}*\Delta\lambda_{em})/\Delta\lambda_{ex} \quad (1).$$

When the respective widths $\Delta\lambda_{ex}$ and $\Delta\lambda_{em}$ of the transmission wavelength bands of the excitation-side filter 11 and the emission-side filter 12 are substantially equal to each other, the following equation is obtained:

$$LF=t_{em}+t_{ex}$$

In other words, when the respective leak factors $t_{ex}$ and $t_{em}$ of the two filters 11, 12 are each about $1\times10^{-5}$, the total leak factor LF is not the same or less since the factor LF is the sum of the leak factors. The leak factor of any multi-layered interferece filter used ordinarily as an excitation-side filter or an emission-side filter is about $1\times10^{-6}$, and is at best about $1\times10^{-7}$.

As described above, regarding the fluorescence imaging apparatus, it is necessary to distinguish the leaking of the filter, from the total leak factor which includes its light source, for discussion. However, it does not appear that description has been made hitherto in the state that the two are distinguished from each other from such a viewpoint. In the present invention, this distinction is made, and presents a method for lowering the total leak factor. In other words, a main object of the invention is to provide a fluorescent image acquiring apparatus wherein a lower total leak factor LF than that of conventional devices is attained while use is made of filters having a performance equivalent to that of filters used at present.

The fluorescence imaging apparatus of the invention is a apparatus comprising: an excitation light source for exciting fluorescence from a sample, a two-dimensional detecting unit for detecting the fluorescence emitted from the sample, an excitation-side filter arranged between the light source and the sample, and an emission-side filter section arranged between the sample and the two-dimensional detecting unit to take out the fluorescence emitted from the sample and lead the fluorescence to the two-dimensional detecting unit. The excitation-side filter is a filter having a transmission wavelength band which causes any light ray having a wavelength in the transmission wavelength band of the emission-side filter to be blocked. The emission-side filter section comprises a multi-layered interferece filter and an absorption filter, and the multi-layered interferece filter and the absorption filter are arranged in series in the direction along which the fluorescence travels. The multi-layered interferece filter and the absorption filter are combined with each other in such a manner that the transmission wavelength band based on the combination contains at least one part of the wavelengths of the fluorescence, and does not contain any transmission wavelength band of the excitation-side filter.

In other words, as a means in which the excitation-side filter and the emission-side filter make it sure not to have a transmission wavelength band in common, the present invention causes a multi-layered interferece filter and an absorption filter to function duplicately as the emission-side filter.

In this fluorescence imaging apparatus, the manner of decreasing the leak light intensity $S_{ex}$ resulting from the emission-side filter is used. In other words, as the emission-side filter section, use is made of an "absorption filter backup means", wherein a multi-layered interferece filter that has been hitherto used is used, and further an absorptive-type filter (which may be referred to merely as an "absorption filter") is arranged in series thereto. When the leak factor of the multi-layered interferece filter is, for example, $1 \times 10^{-5}$, the arrangement of the absorption filter may attain a decrease in the leak factor by three figures. The decrease makes it possible to realize a total leak factor LF of $1 \times 10^{-8}$.

The absorption filter is, for example, a commercially available, inexpensive "colored glass filter". This filter is a filter wherein a light-absorbable substance is dissolved in transparent glass and the absorbable region blocks the transmission of light. A desired absorbable substance may be dissolved and fixed not in glass but in a transparent resin, or in quartz dependently on wavelengths.

Even if multi-layered interferece filters of the same type are used as a backup filter, the leak factor cannot be largely decreased; however, when a multi-layered interferece filter is combined with an absorption filter having a nature different therefrom, characteristics of the two are utilized so that the leak factor can be largely decreased by the multiplication of the leak factors of the two. The reason for this matter or property will be described later. The invention has a feature that the property has been found out so that a large decrease in the total leak factor LF has been attained to improve the fluorescence-detecting precision of a fluorescence imaging apparatus.

The transmittance of the absorption filter is preferably 10% or less in the transmission wavelength band of the excitation-side filter. This means that the leak factor of the absorption filter is 0.1 ($1 \times 10^{-1}$) or less. When the leak factor of the absorption filter is 0.1 or less, the combination thereof with the multi-layered interferece filter makes it possible to decrease the total leak factor by one figure or more. It has been understood that even when a multi-layered interferece filter having a leak factor of about $1 \times 10^{-5}$ is used as a backup filter, the total leak factor is decreased by about only one figure; this matter will be described later. On the other hand, the use of an absorption filter having a leak factor of 0.1 or less makes it possible to decrease the total leak factor more largely than the use of a multi-layered interferece filter as a backup filter.

Furthermore, it is preferred in the invention to use, as the light source, a single-wavelength light source which emits light having wavelengths in a narrower wavelength band than the transmission wavelength band of the excitation-side filter. This manner makes it possible to decrease the leak light intensity $S_{em}$ resulting from the excitation-side filter for a reason described hereinafter. When the emission power of a continuous spectrum light source is regarded as 1, it is supposed that the following intensity is, for example, about $1 \times 10^{-4}$: the light-source-emission light intensity in the transmission wavelength band of the emission-side filter which is present in a wavelength band different from the main wavelengths (meaning a wavelength band in which the emission energy of the single-wavelength light source is concentrated) of excitation light. At this time, the intensity of leak light from the excitation-side filter is about $1 \times 10^{-9}$ in the preferred case described in this paragraph even when the leak factor of the excitation-side filter is about $1 \times 10^{-5}$. In other words, when a single-wavelength excitation light source is used instead of any continuous spectrum light source, light emitted from the light source hardly contains light rays having wavelengths in the transmission wavelength band of the emission-side filter; thus, light rays which have wavelengths in the transmission wavelength band of the emission-side filter and which leak from the excitation-side filter are largely decreased so that the leak factor is substantially decreased.

The reason why the above can be realized will be described in a little more detail with reference to FIGS. 13 to 16.

In FIG. 13(c), $t_{em}$ is considerably large; thus, the $S_{ex}$ emerges noticeably and largely. An effective method for decreasing this is a method of adding an absorption filter 13 (see FIG. 14(b)). Regarding transmission property 43 (see FIG. 14(a)) of the absorption filter 13, the transmittance is small in the transmission wavelength band $\Delta\lambda_{ex}$ of the excitation-side filter 11. The transmittance is represented by $t_a$, and it is presupposed that $t_a$ is, for example, 0.001 ($1 \times 10^{-3}$). In this case, after light from the light source passes through the absorption filter 13, the intensity $S_{ex}$ of the leak light shown in FIG. 14(c) resulting from the emission-side filters 12 and 13 is as follows:

$$S_{ex}=I^*t_{em}^*t_a^*\Delta\lambda_{ex}=L^*t_{em}^*t_a \quad (2)$$

wherein $I^*\Delta\lambda_{ex}$(light source intensity)=L. Thus, the leak light intensity is smaller than the leak light intensity $S_{ex}$ in FIG. 13(c) by the factor $t_a$.

As is evident from FIG. 14(c) also, by the addition of the absorption filter 13, the $S_{ex}$ is decreased but the $S_{em}$ is hardly decreased. This is because a leak of light rays in the transmission wavelength band $\Delta\lambda_{em}$ of the emission-side filter exists in the excitation-side filter 11. In order to decrease the $S_{em}$, it is effective that the continuous spectrum light source 16 such as a tungsten lamp is replaced by a light source (single-wavelength light source) 15 having a narrow main wavelength band as illustrated in FIG. 15. A typical example of the single-wavelength light source is a light emission diode (LED) or a semiconductor laser (LD). A combination of the single-wavelength light source 15 with the excitation-side filter 11 is selected in such a manner that a main wavelength band 51a (the wavelength band thereof is represented by $\Delta\lambda_{LS}$) of emission spectrum 51 of the single-wavelength light source 15 is included in the transmission wavelength band $\Delta\lambda_{ex}$ of the excitation-side filter 11.

Although the wording "single-wavelength light source" is used, precisely, the light source has not only an intense-emission band (main wavelength band) 51a at the center but also a weak-light-emission band at tail regions thereof. The tail regions are related to the leak light $S_{em}$ from the excitation-side filter 11. When the emission intensity of the single-wavelength light source in the main wavelength band thereof, that is, the excitation light intensity is represented by L (=I× $\Delta\lambda_{LS}$) and the emission intensity of the tail regions is represented by the quantity obtained by multiplying I by a factor f[I*f], the intensity $S_{em}$ of the leak light resulting from the excitation-side filter 11 is as follows:

$$S_{em}=L^*f^*t_{ex} \quad (3).$$

The factor "f" is a small value of, for example, 0.001 or 0.0001. Accordingly, the total leak factor LF is:

$$LF=(S_{ex}+S_{em})/L$$

$$=t_a^*t_{em}+f^*t_{ex} \quad (4)$$

A figure obtained by illustrating the expression (4) is FIG. 15(c). The left-side peak $S_{ex}$ is made small by the multiplication of $t_a$. The right-side peak $S_{em}$ is made largely small by the effect of f. When $t_{em}$ and $t_{ex}$ are each i the order of $10^{-6}$ and $t_a$ and f are each in the order of $10^{-3}$, the total leak factor LF is in the order of $10^{-9}$ according to the expression (4) so as to be largely decreased.

As the single-wavelength light source 15, use is made of a laser (a solid laser, a dye laser or a semiconductor laser), or the like. A semiconductor laser (LD) is particularly preferred since the laser is small in size. Besides, a light emitting diode (LED) may also be used. A feature of the laser or LED usable as the single-wavelength light source 15 is that emission energy is concentrated in the transmission wavelength band $\Delta\lambda_{ex}$ of the excitation-side filter 11, and when emitted light is sufficiently weak in the range of wavelengths longer than the band $\Delta\lambda_{ex}$, the discussion about the expression (3) holds true. In order to decrease the total leak factor LF, it is most effective to use, as the emission-side filter, a combined member wherein a multi-layered interferece filter and an absorption filter are arranged in series and further use, as the light source, a single-wavelength light source. However, even when a continuous spectrum light source is used as the light source, a decrease in the intensity $S_{ex}$ of the leak light resulting from the emission-side filter is attained as illustrated in FIG. 14(c), so that the total leak factor LF is decreased. In particular, when $t_{em}$ is considerably larger than $t_{ex}$, the ratio of the leak light intensity $S_{ex}$ resulting from the emission-side filter to the total leak light intensity $(S_{ex}+S_{em})$ is large. Thus, only by the addition of the absorption filter, a large advantageous effect can be obtained.

Examples of the combination of the single-wavelength light source with the absorption filter are given below.

The used absorption filter is a sharp cut filter, and has a characteristic that the filter does not transmit light having short wavelengths and the transmittance of the filter increases toward longer wavelengths. The characteristic is described by a wavelength at which the transmittance turns into 50% in the middle of the increase (the wavelength will be referred to as the 50% transmission wavelength hereinafter). This 50% transmission wavelength is used to give the combination examples.

When the main wavelength band of the single-wavelength light source is in the vicinity of 785 nm, it is preferred that an absorption filter having a 50% transmission wavelength in the range of 830±20 nm is used. When the main wavelength bands of the single-wavelength light sources are in the vicinities of 690 nm, 658 nm, 808 nm, respectively, it is preferred that absorption filters having a 50% transmission wavelength in the following ranges, respectively: 760±20 nm; 720±20 nm; and 850±20 nm, or higher are used. Regarding the 50% transmission wavelength, effective are not only these examples but also wavelengths shorter or longer than each of the examples. It is additionally described herein that effective are also wavelengths in ranges described in the column "Effective range of 50% transmission wavelength of absorption filter" in Table 1 described below.

Of fluorescent dyes containable in a sample which is a target to be detected, indocyanine green is a particularly important substance.

Alternatives to the subject matter by which the invention is specified are inspected herein.

(1) Replacement of the Absorption Filter in the Emission-Side Filter Section with a Multi-Layered Interferece Filter:

It might be expected that when two multi-layered interferece filters combined in-series instead of the proposed series-arrangement of the multi-layered interferece filter and the absorption filter, the leak factor of the emission-side filter section could be a value obtained by multiplying the respective leak factors of the multi-layered interferece filters by each other. Actually, however, the leak factor of the emission-side filter section does not become a small value as expected.

FIG. 16A and FIG. 16B are each a graph showing experimental results of the above-mentioned matter. FIG. 16A shows a case where a tungsten lamp is used as a light source, and FIG. 16B each show a case where an LD (main wavelength band: 785 nm and wavelengths near the wavelength) is used as a light source. In both cases, their multi-layered interferece filters at the excitation side are common to each other. In each of the cases, the optical spectrum of leak light is measured in the case (=A) of arranging, as the emission-side filter section, a single multi-layered interferece filter having a leak factor of $1\times10^{-5}$ in the case (=B) of arranging, as the emission-side filter section, two multi-layered interferece filters arranged in series, the filters each having a leak factor of $1\times10^{-5}$, and in the case (=C) of arranging, as the emission-side filter section, a single multi-layered interferece filter having a leak factor of $1\times10^{-5}$ and a single absorption filter. The right figure of FIG. 16B is a graph obtained by enlarging the transverse axis of a portion of the main wavelength band region in the left figure, and shows the same data as in the left figure.

When the light source is any one of the tungsten lamp and the LD, the light leak is largely decreased by two or three figures in the case where the single multi-layered interferece filter and the single absorption fitter are arranged in series (see C in the concerned graph). However, in the case where the two multi-layered interferece filters are arranged in series (see B in the graph), the light leak is decreased but the width of the decrease is about in the order of one figure. The respective leak factors of the filters are each $1\times10^{-5}$; thus, if the leak factor of the whole were a value obtained by multiplying the leak factors of the individual filters by each other as described above, the leak factor of the whole should be decreased into about $10^{-10}$. Actually, however, the leak factor is decreased only in the order of one figure.

One reason for the above is as follows: The energy of light having wavelengths blocked by any multi-layered interferece filter is not extinguished inside the filter but reflected on the surface thereof. For this reason, when two multi-layered interferece filters are put onto each other, light blocked by the backup filter (out of these filters) goes back and forth many times between the two filters. Every time when the light goes back and forth, light of a quantity corresponding to the leak factor is transmitted through the backup filter. Therefore, light of a quantity corresponding to not less than the leak factor of the backup filter is unfavorably transmitted through the backup filter. Regarding any absorption filter, light to be blocked is not reflected but absorbed therein. Thus, even when an absorption filter is arranged in series to a multi-layered interferece filter, light transmitted therethrough does not go back and forth as described above.

Another reason is that any multi-layered interferece filter is weak against slanting rays. In, for example, the fluorescent image measuring system as shown in FIG. 1, it is necessary to notice that the angle of rays transmitted through the filter 12 at the center of a viewing field in which the emission-side filter section $F_{em}$ arranged near an imaging lens 32 views the sample 31 is different from that at any end of the viewing field. At the center of the viewing field, the inclination of the rays is 0 degree. However, when the viewing angle is 20 degrees, rays at any end of the viewing field are slantingly transmitted through the filter at ±10 degrees. It is a known fact that any multi-layered interferece filter causes a leak of rays radiated slantingly thereinto to increase. Moreover, scattered light based on very small dust necessarily exists. The scattered light is slantingly radiated into and transmitted through the emission-side filter section $F_{em}$, so that the leak factor of the emission-side filter section $F_{em}$ is unfavorably made high. When an absorption filter is combined with the emission-side filter section $F_{em}$, the effect of the scattered light based on dust also becomes small.

(2) Structure Wherein the Emission-Side Filter Section $F_{em}$ is Made Only of (an) Absorption Filter(s):

In FIGS. 17A and 17B are shown experimental results about a case where the emission-side filter section is made of a single absorption filter alone or two absorption filters arranged in series to each other without using any multi-layered interferece filter. In FIG. 17A, a curve IR76 is a curve of the transmittance of the (single) absorption filter (IR76), and a curve F689 is the transmittance property of a multi-layered interferece filter (F689). The vertical axis shows transmittance (%), and the transverse axis shows wavelength (nm). FIG. 17B is a graph of results obtained by making measurements by use of a tungsten lamp as a light source and further using the F689 as an excitation-side filter. In this figure, a curve "EX" is a curve of the spectrum of the light from the tungsten lamp that has been transmitted through only the excitation-side filter F689, that is, the excitation light. A curve "IR76×1" is the spectrum of light transmitted through the absorption filter (IR76), which is only an absorption filter used as the emission-side filter.

A curve "IR76×2" is the spectrum of light transmitted through the two absorption filters (IR76), which are two absorption filters that are arranged, in series, as the emission-side filter.

According to FIG. 17B, in a wavelength band P, the transmitted light intensity of the IR76×1 is decreased by about 4 figures, and the transmitted light intensity of the IR76×2 is further decreased therefrom by a little more than 3 figures. According to this matter, by arranging two filters in series, the leak factor of the whole is close to a value obtained by multiplying the respective leak factors of the filters by each other. However, as is understood from the transmitted light spectrum of the absorption filter IR76 (see FIG. 17A), the light transmission property of the absorption filter is gradual, and is not comparable at all to a sharp light transmission property as shown by a multi-layered interferece filter. Around 690 nm, which is largely apart from the wavelength at which the transmittance is 50%, i.e., 760 nm, light-blocking in the order of 4 figures is attached; however, around the excitation light wavelength band to be blocked, light can be decreased only by about 2 or 3 figures. In general, fluorescence may be emitted from any absorption filter (a swell around 740 nm in FIG. 17B may be based on an effect of the fluorescence). Thus, the use of only (an) absorption filter(s) is small in value. In order not to emit (useless) fluorescence (from the filter(s)), it is the best manner to decrease the light quantity in a wavelength band to be blocked in advance by effect of a multi-layered interferece filter having a sharp light transmission property, and then use an absorption filter, for establishing the multiplication of leak factors, subsidiarily.

As described above, a means that can decrease the leak factor of the whole of the emission-side filter section most effectively is a combination of a multi-layered interferece filter with an absorption filter as a backup filter. This combination makes it possible to compensate for a drawback of the multi-layered interferece filter that "light reflected thereon is intense and the filter is weak against slanting light", and a drawback of the absorption filter that "the blocked light wavelength property is too gradual and the filter emits fluorescence". As the leak factor of the whole, a value close to the product of the leak factors of the two can be gained. The above has been described in the case where the $F_{ex}$ and the $F_{em}$ are typical examples thereof, that is, multi-layered interferece filters. However, even according to an interference filter about which the number of its films is small, the filter produces the "light-blocking ratio improving effect" obtained when an absorption filter is put thereon. Thus, the use thereof in the invention is effective. However, when the number of the films is small, original light-blocking powers of the $F_{ex}$ and $F_{em}$ are low. Thus, a final blocking power obtained when an absorption filter is put thereon lowers in proportion thereto.

An absorption filter cannot be used as the backup filter in the excitation-side filter. As is understood, for example, when the curve 43 in FIG. 15(a) is viewed, the transmitted light property of any absorption filter is a property rising toward the right, that is, "transmission at long wavelengths". Thus, an absorption filter is convenient for the use thereof in the emission-side filter section $F_{em}$. However, when an absorption filter is used as the backup filter in the excitation-side filter, the filter should essentially exhibit a transmitted light property lowering toward the right, that is, "transmission at short wavelengths". However, such an absorption filter does not exist.

It may be considered that a spectroscope (the so-called monochromator) is used instead of the (absorption) filter. A method of using monochromators in a multistage form to make stray light extremely small is known as a different method using a function of the multiplication of leak factors. In a monochromator, a diffraction grating is used to transmit only light of specific wavelengths; thus, when monochromators are used in a multistage form, the multiplication of the leak factors thereof are effected. It is, therefore, possible to use a double-monochromator composed of two monochromators and a triple-monochromator composed of three monochromators to decrease stray light, thereby detecting a feeble fluorescence. However, in any monochromator, light needs to be transmitted through a slit. Thus, "light spread into a surface form" cannot be taken out as an image, as performed in the detection of a fluorescent image. As a result, no monochromator can be used instead of the emission-side filter. Instead of the excitation-side filter, a monochromator may be used; however, the monochromator has a drawback of occupying a larger space than a filter.

In the fluorescence imaging apparatus of the invention, its emission-side filter section is formed to have a multi-layered interferece filter and an absorption filter that are arranged in series in the direction along which fluorescence travels. Therefore, the leak factor of the whole of the emission-side filter section is a value close to the product of the leak factor of the multi-layered interferece filter and that of the absorption filter, so that light leak resulting from the emission-side filter section can be largely decreased. In other words, a high-sensitivity fluorescence imaging apparatus, the whole of which has a good total leak factor, can be realized by an optimal combination which is a combination of a multi-layered interferece filter with an absorption filter while the used filters are filters each having a leak factor at a level of $10^{-5}$ to $10^{-6}$, which can be obtained by an ordinary technique, or a leak factor worse than it.

BRIEF DESCRIPTION OF THE DRAWINGS

FIG. 6(a) shows a case where no absorption filter is present, FIG. 6(b) shows a case where the absorption filter is present, FIG. 6(c) is a chart showing the (light) intensity at the sectional center of the image (a) in the transverse direction, FIG. 6(d) is a chart showing the (light) intensity at the sectional center of the image (b) in the transverse direction, and FIG. 6(e) is a perspective view illustrating a measured sample.

FIG. 13(a) is a waveform chart showing a light source spectrum and the wavelength property of the multi-layered interferece filter, FIG. 13(b) is an arrangement chart showing an arrangement of the light source, an excitation-side filter and an emission-side filter, and FIG. 13(c) is a waveform chart showing the wavelength distribution of the leak light after light passes through the two filters.

FIG. 14(a) is a waveform chart showing a light source spectrum, and the wavelength properties of the multi-layered interferece filter and the absorption filter, FIG. 14(b) is an arrangement chart showing an arrangement of the light source, the excitation-side filter, the emission-side filter and the absorption filter, and FIG. 14(c) is a waveform chart showing the wavelength distribution of the leak light after light passes through all the filters.

FIG. 15(a) is a waveform chart showing a light source spectrum, and the wavelength properties of the multi-layered interferece filter and the absorption filter, FIG. 15(b) is an arrangement chart showing an arrangement of the light source, the excitation-side filter, the emission-side filter and the absorption filter, and FIG. 15(c) is a waveform chart showing the wavelength distribution of the leak light after light passes through all of the filters.

FIG. 16B The figures are each a waveform chart showing the wavelength distribution of leak light when a single-wavelenght light source is used and two multi-layered interferece filters are put onto each other, and the right figure is a figure obtained by enlarging the transverse axis in the left figure.

FIG. 17A The figure is a waveform chart showing the transmission wavelength property of an absorption filter alone, and a waveform chart showing the transmission wavelength property of a multi-layered interferece filter for selecting noticed wavelengths.

DESCRIPTION OF THE REFERENCE NUMERALS

Figure 1:
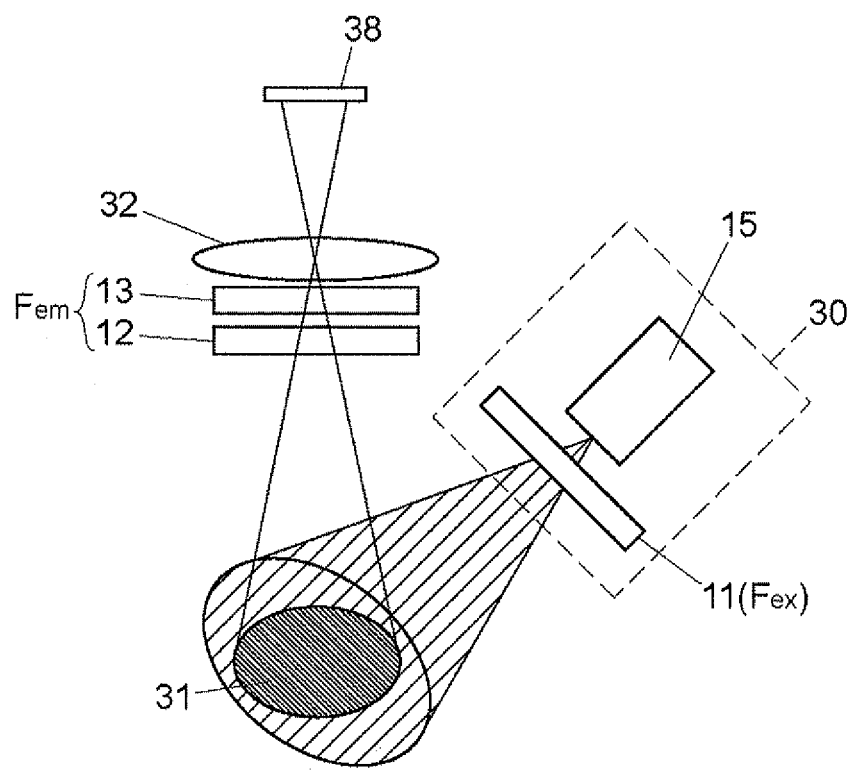
FIG. 1 The figure shows an example wherein the invention is applied to a system for measuring fluorescence from a macro sample.

11($F_{ex}$) excitation-side filter
$F_{EM}$ emission-side filter section
12 emission-side multi-layered interferece filter
13 absorption filter
15 single-wavelength light source
16 continuous spectrum light source
22 lateral radiation spectrum of single-wavelength light source
28 main wavelength band of single-wavelength light source
30 radiating unit
31 sample
32 image-forming lens
38 two-dimensional detecting unit
41 transmission wavelength property of excitation-side multi-layered interferece filter
42 transmission wavelength property of emission-side multi-layered interferece filter
42a short wavelength part of transmission band of emission-side multi-layered interferece filter
43 transmission wavelength property of absorption filter
50 radiation spectrum of continuous spectrum light source
51 radiation spectrum of single-wavelength excitation light source
51a central spectrum of single-wavelength excitation light source 51b part of lateral radiation spectrum of single-wavelength excitation light source, the part being included in transmission wavelength width of fluorescence detecting filter

DETAILED DESCRIPTION OF THE INVENTION

Example 1

FIG. 1 is a view illustrating an example of the fluorescence imaging apparatus of the invention.

Figure 12:
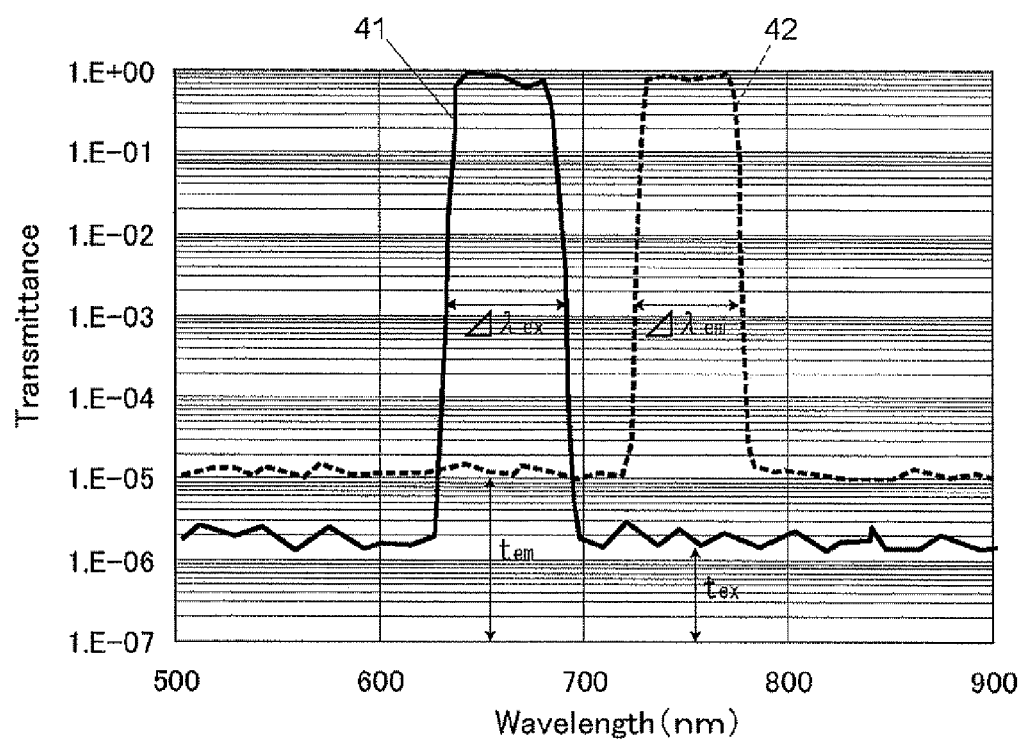
FIG. 12 The figure is a waveform chart showing a typical transmission property example of a multi-layered interferece filter at each of the excitation side and the emission-side (of the concerned apparatus).

The apparatus has a radiating unit 30 for exciting a sample 31 to generate fluorescence. The radiating unit 30 is equipped with a light source 15, and an excitation-side filter 11 for removing, from light rays from the light source 15, light rays not used as excitation light. The excitation-side filter 11 is, for example, a multi-layered interferece filter, and is formed to have a light transmission property 41 shown in FIG. 12, and sufficiently transmit light having a wavelength in a main wavelength band of the light source 15 while blocking light having any longer wavelength than it, in particular, light having any wavelength in the wavelength band corresponding to the fluorescence. The transmittance of the excitation-side filter 11 is about $10^{-6}$ in the band of wavelengths to be blocked by the excitation-side filter 11.

The fluorescence emitted from the sample passes through an emission-side filter section $F_{em}$ to form an image on a two-dimensional detecting unit 38 made of a CCD camera or the like through an imaging lens 32. In the two-dimensional detecting unit 38, a fluorescent image of the sample, which is a target living body, is obtained. The emission-side filter section $F_{em}$ is a section wherein a multi-layered interferece filter 12 and an absorption filter 13 are arranged in series in the traveling direction of the fluorescence. The multi-layered interferece filter 12 has, as a transmission wavelength band thereof, a wavelength band including wavelengths of the fluorescence, and is formed to block light having a wavelength in other wavelength bands, in particular, in a wavelength band corresponding to the excitation light. The transmittance (leak factor) in the blocked wavelength band is about $1 \times 10^{-6}$. The absorption filter 13 is formed to transmit light of long wavelengths containing the wavelength band corresponding to the fluorescence, and block light having a wavelength in the wavelength band corresponding to shorter wavelengths than the long wavelengths, in particular, in the wavelength band corresponding to the excitation light. The transmittance (leak factor) in the blocked wavelength band is about $1 \times 10^{-3}$. As described above, the series-arrangement of the multi-layered interferece filter 12 and the absorption filter 13 make the leak factor of the emission-side filter section $F_{em}$ substantially into the product of the leak factor of the multi-layered interferece filter 12 and that of the absorption filter 13. Thus, the whole of the emission-side filter section $F_{em}$ has a leak factor in the order of $10^{-9}$.

Figure 2A:
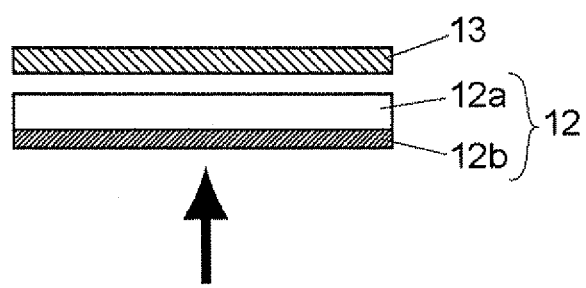
FIG. 2A The figure is an explanatory view illustrating the structure of an emission-side filter.
Figure 2B:
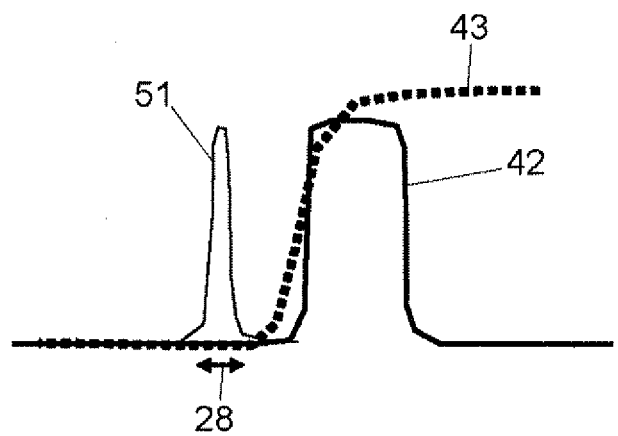
FIG. 2B The figure is a waveform chart when the selection of the property of an absorption filter is proper.
Figure 2C:
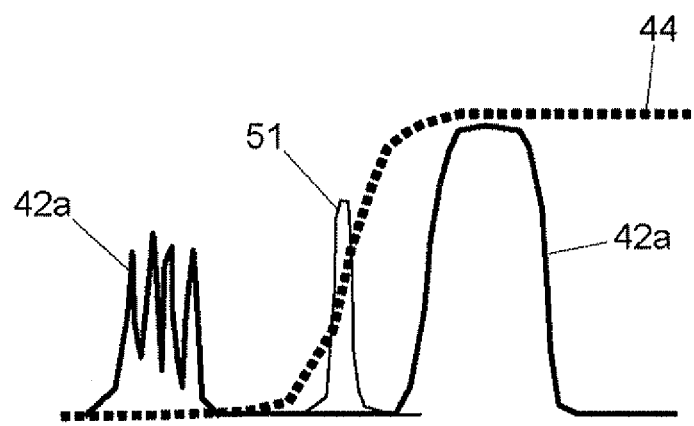
FIG. 2C The figure is a waveform chart when the selection of the property of an absorption filter is improper.

As illustrated in FIG. 2A, the emission-side filter $F_{em}$ is composed of the multi-layered interferece filter 12 and the absorption filter 13, and the multi-layered interferece filter 12 is composed of a transparent support 12a and a multilayered interference film 12b. The multilayered interference film 12b, the transparent support 12a and the absorption filter 13 are preferably formed in such a manner that light from the sample passes through the film 12b, the support 12a and the filter 13 in this order, as represented by an arrow for the following reason: according to this order, even when the transparent support 12a or the absorption filter 13 emits fluorescence, light weakened by the multilayered interference film 12b passes through the transparent support and the absorption filter so that the fluorescence is weakened. Naturally, it is preferred that the materials of the transparent support 12a and the absorption filter 13 are each a material which emits a small fluorescence quantity from itself. As for the absorption filter 13, it is necessary that the transmission property of the main wavelength band 28 of the emission spectrum 51 of the light source 15 is sufficiently small as represented as a transmission wavelength property 43 in FIG. 2B. Regarding the light transmission property 42 of the multi-layered interferece filter 12 as well, the light transmittance in the main wavelength band 28 is sufficiently small. Thus, the multi-layered interferece filter 12 and the absorption filter 13 duplicately prevent scattered light of the excitation light from leaking toward the two-dimensional detecting unit 38. In FIGS. 2(a) to 2(c), the multi-layered interferece filter 12 and the absorption filter 13 are separated from each other. However, these may be formed into a single filter wherein these are bonded onto each other through an adhesive. Furthermore, use may be made of a method of forming the multilayered interference film 12b onto the absorption filter itself by vapor deposition without using the transparent support 12a. Two absorption filters may be stacked onto the rear of the multi-layered interferece filter 12. An advantageous effect of the stacking of the two is equivalent to that of an increase in the thickness of the (single) absorption filter; however, the transmittance falls slightly in the fluorescence wavelengths. In other words, it is allowable to adjust the thickness and/or the number of the absorption filter(s) in order to select a good compromise between the adjustment of the blocking ratio at required blocking wavelengths and the efficiency of capturing the fluorescence.

A filter is commercially available wherein an absorption filter having a transmission wavelength property as represented by reference number 44 in FIG. 2C is synthesized with a multi-layered interferece filter. However, as is evident from the curve 44, this absorption filter hardly blocks light having a wavelength in the main wavelength band of the light source 15. In any multi-layered interferece filter, a transmission band as represented by the reference number 42a may make its appearance at short wavelengths; the absorption filter is synthesized with the multi-layered interferece filter in order to "cut out" this transmission band. The absorption filter required as the emission-side filter section $F_{em}$ in the invention is not such a filter for "cutting out" the short-wavelength-transmission band, and has a property that the filter is combined with the multi-layered interferece filter to block a radiation 51a from a single-wavelength light source duplicately.

Figure 16A:
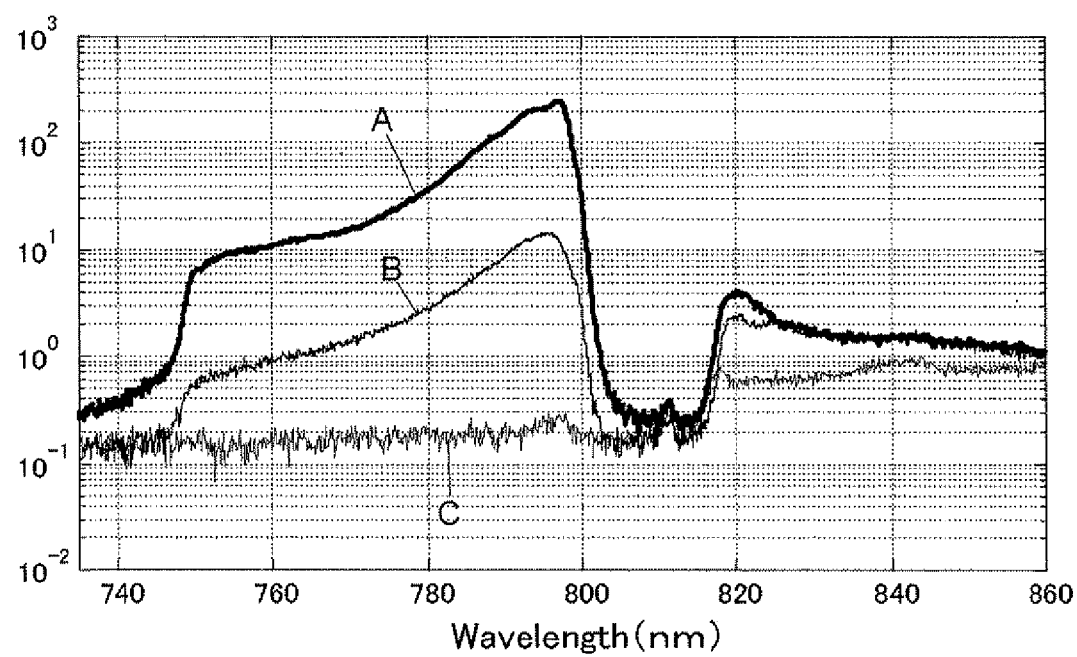
FIG. 16A The figure is a waveform chart showing the wavelength distribution of leak light when a continuous spectrum light source is used and two multi-layered interferece filters are put onto each other.
Figure 17B:
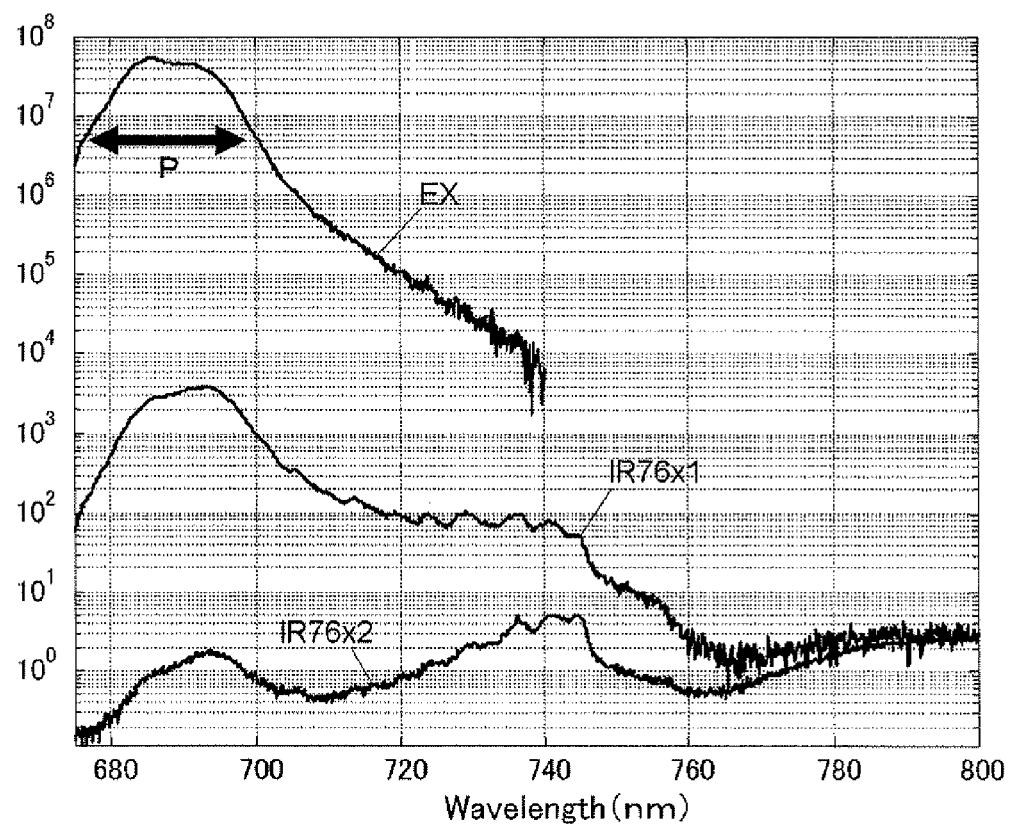
FIG. 17B The figure is a waveform chart showing an excitation light spectrum, and the spectrum of the light after the light passes through a single absorption filter or two absorption filters.

A description is herein made as to what degree an absorption filter having a transmission wavelength property, as represented by reference number 43, causes the spectrum 51 of the light source 15 to weaken so that this absorption filter can exhibit an effective reinforcing power. As described above with reference to FIG. 16, in the case of arranging two multi-layered interferece filters in series, the leak factor of the whole of the emission-side filter section $F_{em}$ can be decreased by about only one figure. Accordingly, when the reinforcing power (leak factor) of the absorption filter is about 10% or less, the absorption filter produces a larger advantageous effect than the multi-layered interferece filters.

Figure 3:
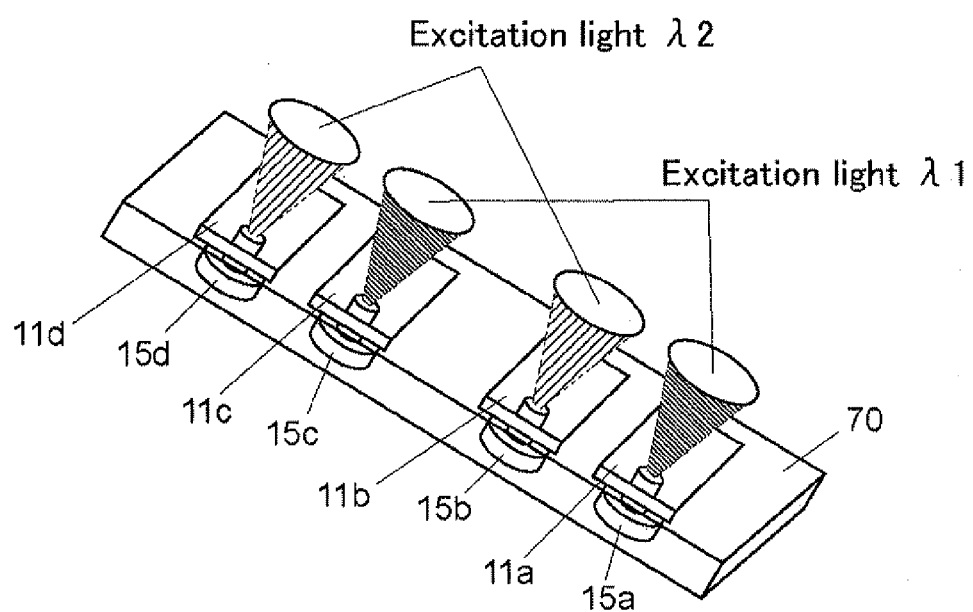
FIG. 3 The figure is a perspective view illustrating an example of an excitation light radiating device.

The following describes an example of the light source 15 with reference to FIG. 3.

A light source device 30 has four LDs 15a to 15d on a light-source-attaching base 70. The light-source-attaching base 70 is a plate-form holder extended at length in a direction parallel to the body axis of a small animal as the sample. The four LDs 15a to 15d are arranged in the direction of the body axis of the small animal. In this example, the LDs 15a and 15c emit light having the same wavelength (for example, 785 nm). The other two LDs 15b and 15d emit light having the same wavelength (for example, 690 nm). Excitation-side filters 11a to 11d are attached to the four LDs 15a to 15d, respectively, so as to be put thereon. The four pairs of the laser diodes and the excitation-side filters make it possible to radiate their respective excitation light rays to the sample.

As described above, such LDs each give radiation having a small intensity also in wavelength bands of tails of the emission wavelength band (main wavelength band) thereof in many cases. The radiation intensity from the tail regions is 0.001 ($10^{-3}$) (called a factor f) or less than the radiation intensity from the main wavelength band. When the transmittance of the excitation-side filter in the fluorescent wavelength band is about $1\times10^{-6}$, the emission intensity of the LDs in this fluorescent wavelength band is the value "the emission intensity in the main wavelength band×f" or less. Thus, the intensity of leak light from the excitation-side filter in the fluorescence wavelength band can be controlled into the value "the transmission light intensity in the main wavelength band×$10^{-9}$" or less.

Figure 7:
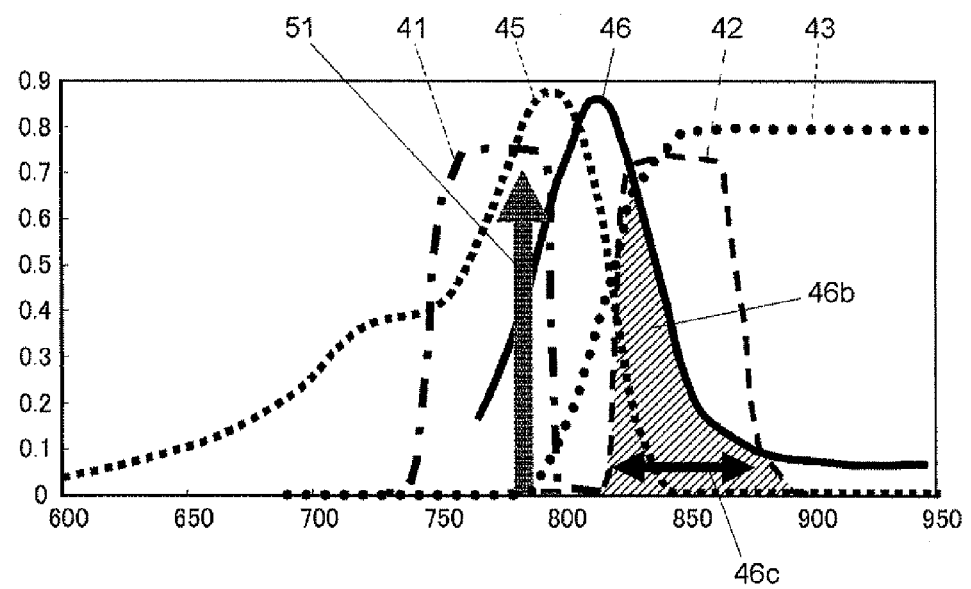
FIG. 7 The figure is a waveform chart showing the wavelength property of a fluorescent dye, ICG, and further shows wavelength properties of a light source and a filter when ICG is target.

The radiating unit 30 in FIG. 3 makes it possible to change the wavelengths of excitation light therefrom, change excitations along plural directions, perform optional simultaneous excitation, and select some other freely without using any mechanical mechanism by controlling the lightings of the LDs arranged in the different positions independently. Thus, a new finding of the existing position of a fluorescent molecule to be detected can also be obtained. In general, the LDs and the excitation-side filters 11 paired therewith each have a size 1 cm or less square; thus, such a lighting unit has an advantage that many different light sources can be arranged in a relatively small space. In the radiating light source 30 in FIG. 3, inexpensive LEDs may be used instead of the LDs. The laser diodes or the light emitting diodes have an effect of restraining stray light. Additionally, the diodes emit no light in a useless wavelength band, and further give a large intensity at a unit wavelength width. Therefore, the case of the diodes can give more intense excitation light than a case where an excitation filter is combined with a halogen lamp to select wavelengths. Thus, it can be pointed out that the diodes further have secondary advantages of contributing to a reduction in the period for measurement or an improvement in the sensitivity of measurement.

solution thereof is sold for the inspection of liver function. It is expected that ICG will be used also as fluorescence-labeling agent for observing the behavior of the inside of a living body and the recognition degree thereof will be heightened hereafter. In FIG. 7, reference number 45 represents the excitation spectrum of ICG; 46, the fluorescence spectrum of ICG; 51, an imaged emission spectrum of an LD (wavelength: 785 nm), which is represented by an arrow; 41, the light transmission spectrum of an excitation-side filter, by effect of which 800-nm-or-more-wavelength lateral radiated-light that exists in the emission spectrum of the LDs is removed; 42, the light transmission spectrum of the multi-layered interferece filter constituting the emission-side filter section; and 43, the light transmission spectrum of an absorption filter (backup filter) constituting the emission-side filter section. By combining the members 42 and 43 with each other, the leak light of the emission wavelengths of the LD can be controlled into an extremely small value. A synthetic transmission band 46c of the members 42 and 43 is a part of long wavelengths in the whole 46 of the fluorescence spectrum of ICG, and corresponds to only a capturing range of about 40 to 50% of (the range of) the entire emission spectrum. However, in order to make the detection sensitivity of the fluorescence high, it is overwhelmingly more important to remove leak light in this range than to capture the whole 46 of the fluorescence. Since the intensity of a laser or the sensitivity of a detecting unit has a sufficient margin (for example, about 2 figures), a small decline in the capturing ratio of the fluorescence spectrum can easily be covered with the capacity thereof. Thus, no problem is caused. In this sense, the band 46c is referred to as the "usable wavelength band of light emitted from dye", which is distinguished from the whole 46 of the emission spectrum wavelength band of the fluorescence. In this example, this band is in the range of 830 to 880 nm.

Figure 8:
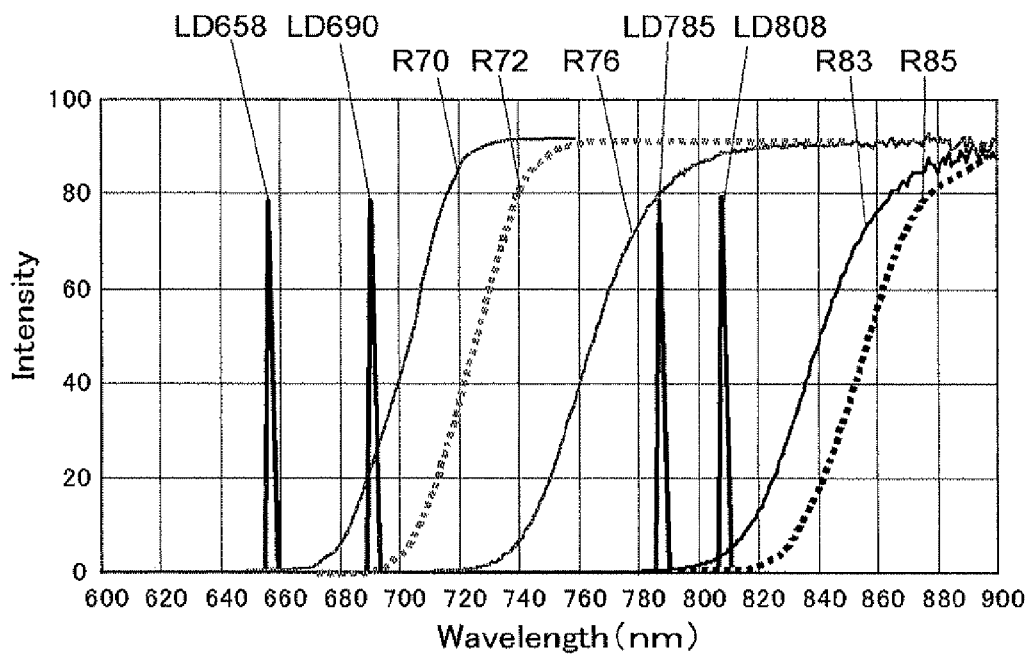
FIG. 8 The figure is a waveform chart showing combinations in each of which a wavelength of a usable LD is combined with (the wavelength property of) an actual absorption filter.

Similarly, regarding other dyes, the same examination as with ICG in FIG. 7 are made, and the results are summaries. The resultant combinations of respective wavelength properties of "the light source, the excitation-side filter and the emission-side filter" are shown in Table 1. It can be mentioned that Table 1 shows examples of the application of the invention to some dyes. Wavelength properties of semiconductor laser (LDs) and absorption filters in this table are shown in FIG. 8.

TABLE 1

| Detected dye | LD | Laser wavelength | Excitation-side multi-layered interferece filter | Emission-side multi-layered interferece filter | Absorption filter | 50% Transmission wavelength of absorption filter | Usable wavelength band of light emitted from dye |
|---|---|---|---|---|---|---|---|
| Cy5.5, quantum dots, and others | 658-nm band LD | 658 nm ± 10 nm | Blocking of wavelengths of 670 nm or more | Blocking of wavelengths of 690 nm or less | R70 or R72 | 720 nm ± 20 nm | 700-750 nm |
| Cy7, quantum dots, and others | 690-nm band LD | 690 nm ± 10 nm | Blocking of wavelengths of 740 nm or more | Blocking of wavelengths of 770 nm or less | IR76 | 760 nm ± 20 nm | 770-830 nm |
| ICG, quantum dots, and others | 785-nm band LD | 788 nm ± 10 nm | Blocking of wavelengths of 800 nm or more | Blocking of wavelengths of 820 nm or less | IR83 | 830 nm ± 20 nm | 830-880 nm |
| ICG, quantum dots, and others | 808-nm band LD | 808 nm ± 10 nm | Blocking of wavelengths of 825 nm or more | Blocking of wavelengths of 840 nm or less | IR85 | 850 nm ± 20 nm | 850-900 nm |

With reference to FIG. 7, the following describes a combination of respective wavelength properties of a light source, an excitation-side filter and an emission-side filter section in the case of using a fluorescent dye, indocyanine green (hereinafter abbreviated to ICG) as a typical target to be measured.

ICG is well known as a dye emitting fluorescence in a near infrared band of 800 nm or more, and further a parenteral 4 types (LD658, LD690, LD785 and LD808) of the LDs are shown. These are semiconductor lasers of a 658 nm band, an LD690 band, an LD785 band, and an LD808 band, respectively. Regrettably, wavelengths of LDs put into practical use are not freely selected, and LDs totally giving discontinuous wavelengths are supplied. Of the supplied LDs, LDs giving wavelengths of 658±10 nm, LDs giving wavelength of 690±10 nm, LDs giving wavelengths of 785±10 nm, LDs giving wavelengths of 808±10 nm are inexpensive, and supplied in a great quantity. Thus, the expression of 658 nm band, 690 nm band, and the like are used to show the LDs in Table 1. 5 types of the absorption filter, R70, R72, IR76, IR83 and IR85 are shown. These are glass filters supplied as sharp cut filters from Hoya Candeo Optronics Corporation. Similar filters are also supplied from Schott AG in Germany. LD658 is combined with R72, and further LD690, LD785 and LD808 are combined with IR76, IR83 and IR85, respectively. A selection may be made to combine LD658 with R70. These sharp cut filters are usually specified by the wavelength at which the transmittance is 50%, and are each designated in such a manner that the 50% transmission wavelength thereof is XXX nm. Thus, in Table 1, the absorption filters are each specified by the 50% transmission wavelength thereof. An effective range of the 50% transmission wavelength of each of the absorption filters has a width. The short wavelength part thereof is a 10% transmission range in which the wavelength of the (combined) LD can be blocked, and the long wavelength part is decided by the condition that the transmittance is not extremely lowered in the range of usable wavelengths of each of the dyes, which is shown in the right end column of the table, out of fluorescence emission wavelengths of the dye. Each effective range selected from this consideration is described in the "Effective range of 50% transmission wavelength" column. These combinations are tabled and shown together with the fluorescent dyes that are measuring targets.

Figure 5A:
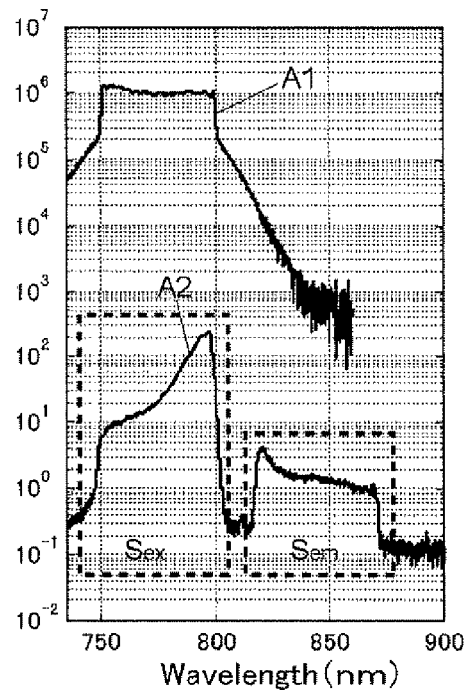
FIG. 5A The figures are each a chart showing a leak light spectrum according to the presence of an absorption filter or the absence of any absorption filter in a case where a continuous spectrum light source is used, and the left figure and the right figures are figures when no absorption filter is present and when the absorption filter is present, respectively.
Figure 5A:
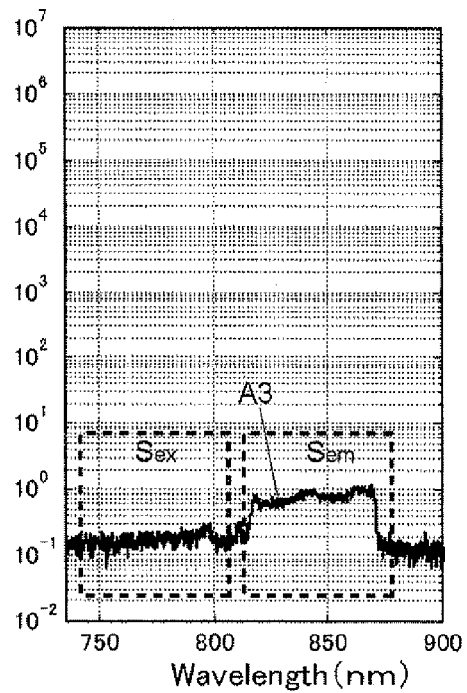
Figure 5B:
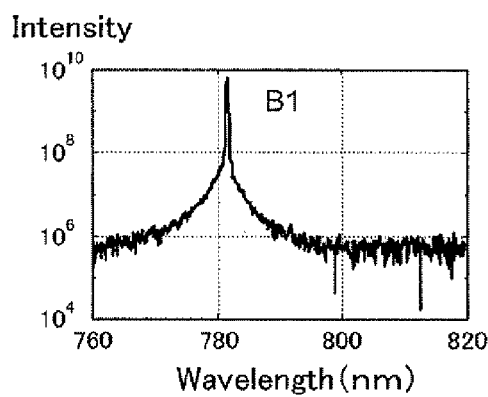
FIG. 5B The figures are each a chart showing a leak light spectrum according to the presence of an absorption filter or the absence of any absorption filter in a case where a single-wavelength light source is used, the upper figure shows the spectrum of the light source, and the lower left figure and the lower right figure are figures when no absorption filter is present and when the absorption filter is present, respectively.
Figure 5B:
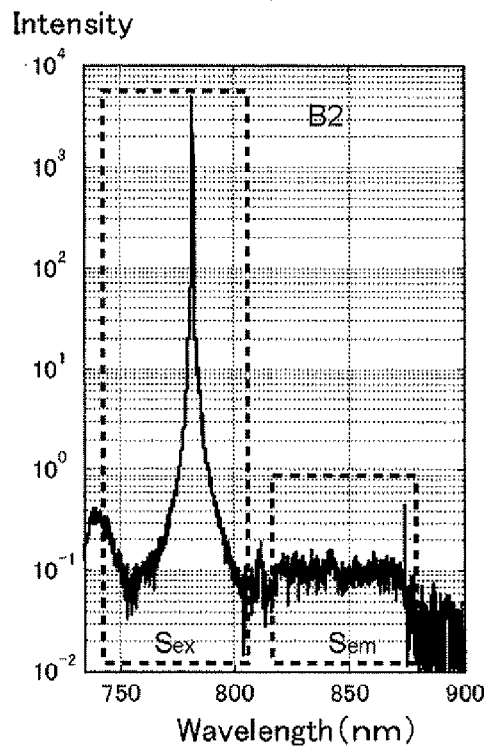
Figure 5B:
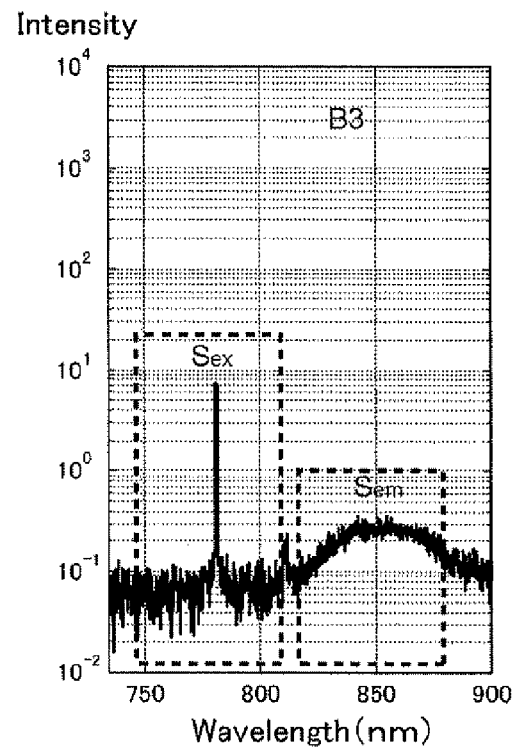
Figure 13:
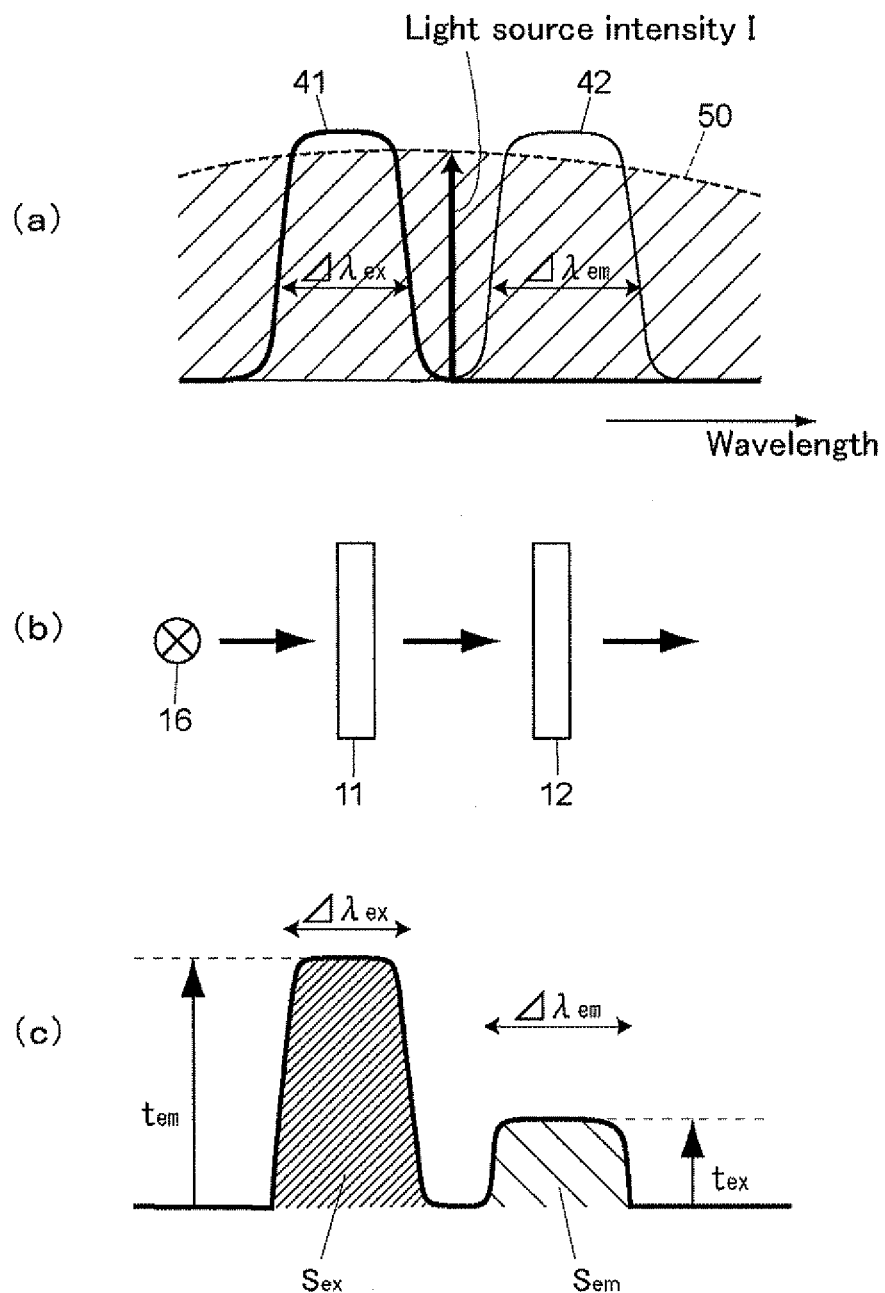
FIG. 13 The figures are charts for explaining a typical wavelength distribution of leak light that has passed through a multi-layered interferece filter of a conventional type.
Figure 15:
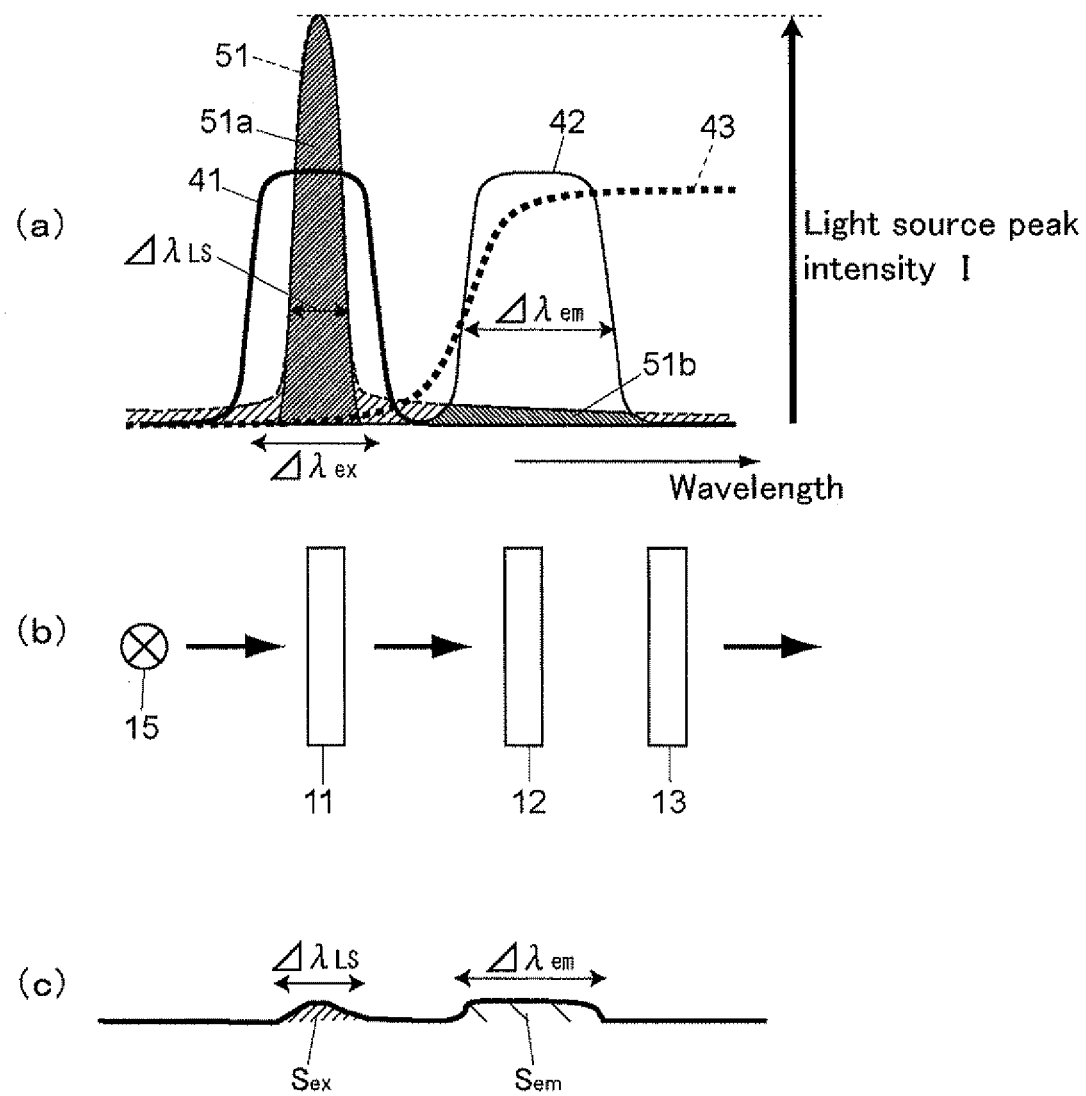
FIG. 15 The figures are charts for explaining a decrease in leak light when the absorption filter is added, and further, the light source is changed to a single-wavelength light source.

FIGS. 5A and 5B are graphs of actual measured data about the leak-light-decreasing effect. FIG. 5A shows a case where a tungsten lamp is used as a light source, and FIG. 5B shows a case where an LD is used as a light source. In FIG. 5A, a curve A1 is the spectrum of excitation light therefrom, a curve A2 is the spectrum of the light when no absorption filter is arranged in the emission-side filter section $F_{em}$, that is, the spectrum of the light that has passed through the filter 12 in FIG. 13(b), and a curve A3 is the spectrum of the light when an absorption filter is arranged in the emission-side filter section $F_{em}$, that is, the spectrum of the light that has passed through the filter 13 in FIG. 15(b).

Figure 14:
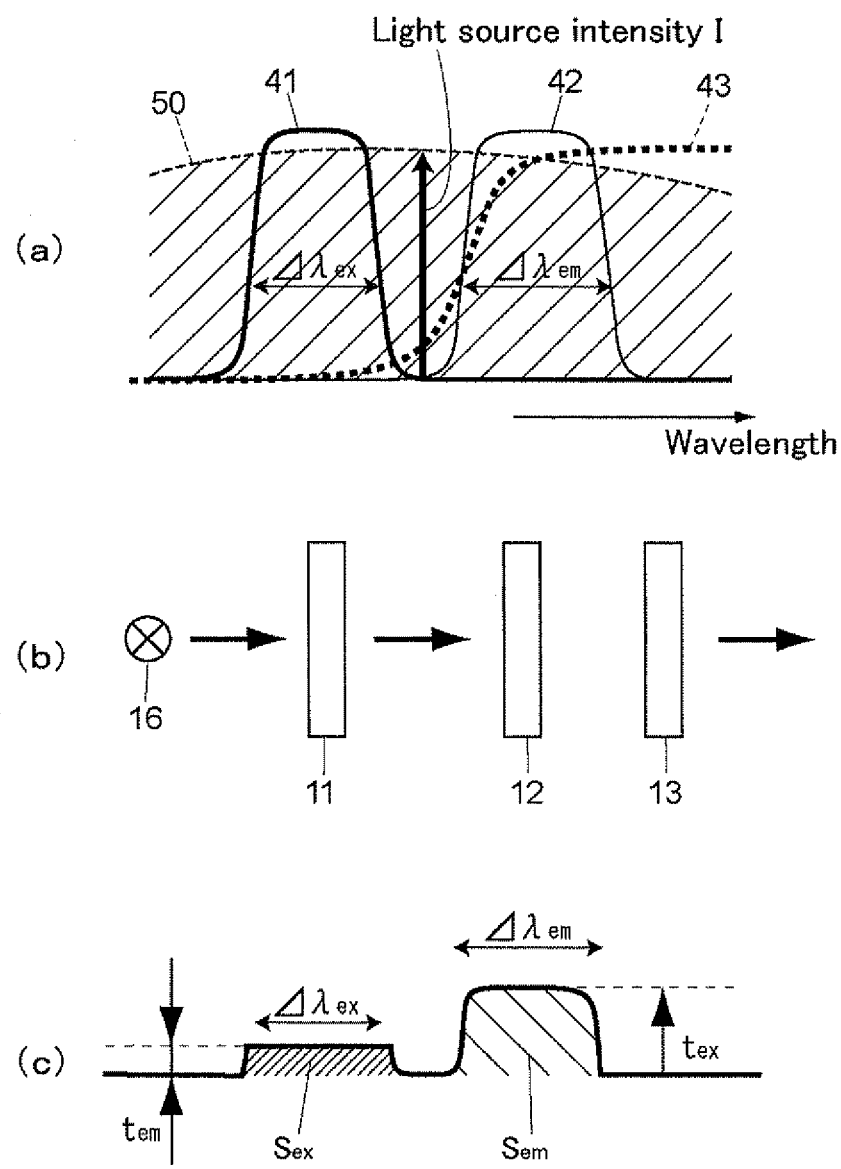
FIG. 14 The figures are charts for explaining the wavelength distribution of leak light when an absorption filter is added to the system in FIG. 13.

On the curve A2, peaks corresponding to $S_{ex}$ and $S_{em}$ are formed. The peak $S_{ex}$ is smaller than the excitation light intensity by about 4 or 5 figures. However, a considerably large leak quantity is generated. Against this, the peak $S_{em}$ is smaller than the excitation light intensity by about 6 figures, and $S_{em}$ is about 1/30 of $S_{ex}$. The curve A3 in the right side corresponds to the case shown in FIG. 14, wherein the excitation light is further passed through the absorption filter. The light-blocking effect of the absorption filter is well effective, so that $S_{ex}$ is lowered by 2 or more figures, so as to turn very small. Conversely, the $S_{em}$ turns more conspicuous. The reason why $S_{em}$ is not reduced by much is that the radiation intensity of the continuous spectrum light source is large in the wavelength range of the $S_{em}$.

The curve B1 is the spectrum of the excitation light, and the intensity of its peak region is a large value of about $10^{10}$. When the light passes through the multi-layered interferece filter at the emission-side, the intensity turns about $10^4$ as represented by the curve B2. In other words, the multi-layered interferece filter makes the intensity lower by 6 figures. However, the peak $S_{ex}$ is larger than the peak $S_{em}$ by 3 figures or more.

Finally, regarding the curve B3, which is obtained by measurement in the state that the absorption filter is added, the peak of the laser is lowered into about a little less than 10 in intensity. Thus, the intensity is lower than the original value, $10^{10}$, by nearly 9 figures. The $S_{em}$ swells slightly, so that $S_{em}$ is slightly increased from $S_{em}$ in the case of the B2; this matter appears to be based on fluorescence emitted by the absorption filter itself. However, the intensity thereof is at a low level. The calculated value of the area of each of the peaks $S_{ex}$ and $S_{em}$ in each of the concerned figures is shown in Table 2. Table 2 shows numerical values of the leak light intensity in each of the concerned cases. According to this table, $S_{ex}$ when no absorption filter is set is 3000 in the case of tungsten excitation, and is about 2200 in the case of LD excitation. It is well understood that larger leak is generated in the cases than in the other cases.

TABLE 2

|  | Light source radiation intensity L |  | Excitation-side wavelength leak light intensity $S_{ex}$ | Detected Fluorescence wavelength leak light intensity $S_{em}$ |
|---|---|---|---|---|
| Tungsten Lamp excitation | 5.48E+07 | Without absorption filter | 3006.9 | 90.4 |
|  |  | With absorption filter | 11.3 | 44.7 |
| LD excitation | 2.63E+09 | Without absorption filter | 2257.3 | 6.3 |
|  |  | With absorption filter | 8.1 | 13.6 | section $F_{em}$, that is, the spectrum of the light that has passed through the filter 13 in FIG. 14(b). In FIG. 5B, a curve B1 is the spectrum of excitation light therefrom, a curve B2 is the spectrum of the light passing through $F_{em}$ when no absorption filter is arranged in the emission-side filter section $F_{em}$, and a curve B3 is the spectrum of the light when an absorption filter Table 3 shows calculation examples of the leak factors calculated from the values in Table 2. The leak factors are each a ratio obtained by making a calculation using, as a denominator, the radiation intensity L obtained by integrating A1 or B1, and using, as a numerator, the intensity of each of the leak lights.

TABLE 3

|  |  | Excitation wavelength leak factor ($S_{ex}$/L) | Detected Fluorescence wavelength leak factor ($S_{em}$/L) | Total leak factor ($S_{ex} + S_{em}$)/L |
|---|---|---|---|---|
| Tungsten Lamp excitation | Without absorption filter | 5.49E−05 | 1.65E−06 | 5.65E−05 |
|  | With absorption filter | 2.06E−07 | 8.15E−07 | 1.02E−06 |
| LD excitation | Without absorption filter | 8.58E−07 | 2.40E−09 | 8.61E−07 |
|  | With absorption filter | 3.08E−09 | 5.15E−09 | 8.23E−09 |

When no absorption filter is set, the excited wavelength leak factor is $5 \times 10^{-5}$ in the case of the tungsten lamp excitation, and that is $8 \times 10^{-7}$ in the case of the LD excitation. When the absorption filter is set up, the former factor is improved to $2 \times 10^{-7}$, and the latter factor is improved to $3 \times 10^{-9}$; the total leak factors are also improved to $1 \times 10^{-6}$ and $8 \times 10^{-5}$, respectively. The matter that the decrease in the total leak factor is restrained to $1 \times 10^{-6}$ when the tungsten lamp is used as the light source is based on the fact that the light leak at the emission-side is not decreased. However, by effect of the absorption filter, the total leak factor turns into 1/50; thus, it can be mentioned that even when no laser is used, a considerably useful result is obtained. This is because the maximum factor of the (total) light leaks is the "leak at the excitation side". As described herein, the absorption filter first takes effect so that the total leak factor is lowered. The factor is further lowered by use of a single-wavelength light source.

Figure 6:
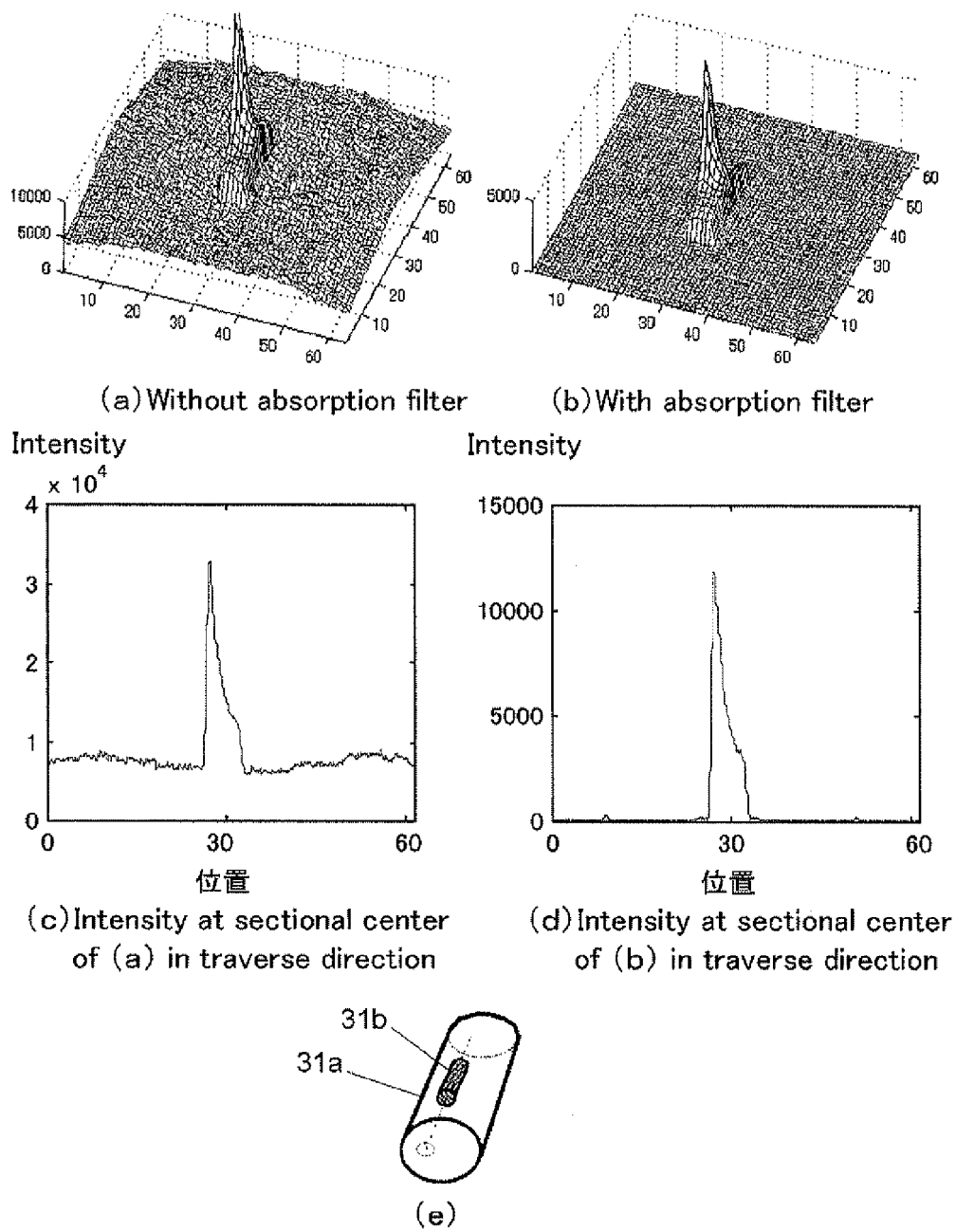
FIG. 6 The figures each show image data showing an actual example of advantageous effects of an absorption filter.

Next, in FIG. 6 is shown an example which clearly shows the advantageous effect of an absorption filter when an image is gained. To compare the image performances (leaks each resulting from a shortage in the light-blocking power at the emission side) based on the presence and the absence of an absorption filter with each other under conditions that the leak $S_{em}$ resulting from the excitation side is lowered using an LD light source. The samples are each a sample as illustrated in FIG. 6(*e*), wherein a short tube 31*b* filled with a solution of ICG, which is a fluorescent dye, is buried in a circularly-columnar milky white resin 31*a* at a slightly left position from the center of the resin. Fluorescence from the milky white resin itself and fluorescence from ICG at the position left from the center should be detected.

FIG. 6(*a*), which is the upper left figure of FIG. 6, shows an image obtained when no absorption filter is arranged. FIG. 6(*b*), which is the upper right figure thereof, shows an image obtained when an absorption filter is arranged. When no absorption filter is arranged as illustrated in the left figure, FIG. 6(*a*), a large quantity of leak light is generated over the whole of the image screen, so that an uneven background emerges remarkably. Thus the outline of the fluorescence from the milky white resin cannot be vividly captured. However, in the right figure, FIG. 6(*b*), leak light is generated in a small quantity so that a background (as described above) is not substantially generated so that the fluorescence from the milky white resin and the fluorescence from ICG can be vividly captured. Graphs (c) and (d) below these images (a) and (b) are graphs obtained by plotting, in the transverse direction, the respective light intensities detected at sectional centers of the upside images. In the left figure, FIG. 6(*a*), the background (leak light) reaches 20% of a central signal from the sample. However, in the right figure, FIG. 6(*b*), the background falls substantially into a zero level. Thus, the sample can be detected without being buried in the background.

Example 2

Figure 4:
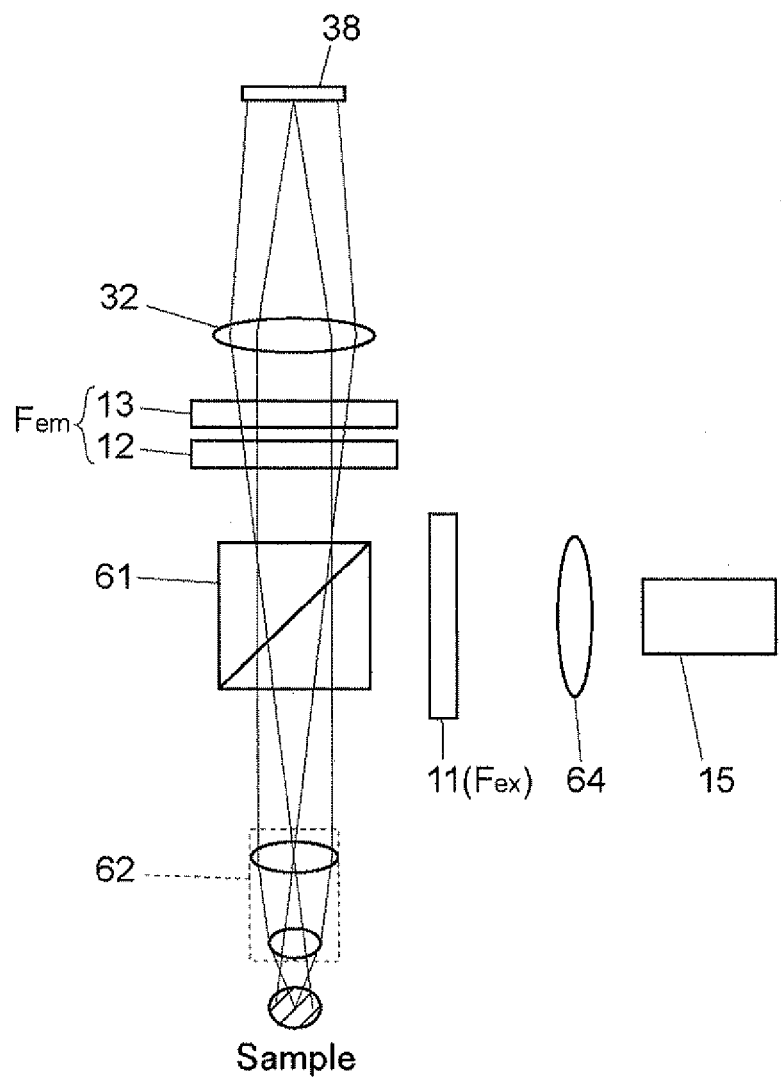
FIG. 4 The figure is a schematic structural view of an example wherein the invention is applied to a system for measuring fluorescence from a micro sample.

With reference to FIG. 4, a description is made about a case where the invention is applied to a micro sample, for which a microscope is used.

The system in this figure is not substantially varied from ordinary fluorescence microscopes. In the fluorescence microscope, an important member for functions of the excitation side and the emission-side is a rectangular beam splitter 61 wherein two prisms are caused to adhere onto each other. Toward two surfaces thereof are arranged an excitation-side filter 11 ($F_{ex}$) and an emission-side filter section ($F_{em}$) paired therewith. This fluorescence microscope is different from conventional fluorescent microscopes in that the emission-side filter section ($F_{em}$) is composed of a multi-layered interferece filter 12 and an absorption filter 13. A light source 15 is a single-wavelength light source; however, the light source 15 may be a continuous spectrum light source.

Figure 9:
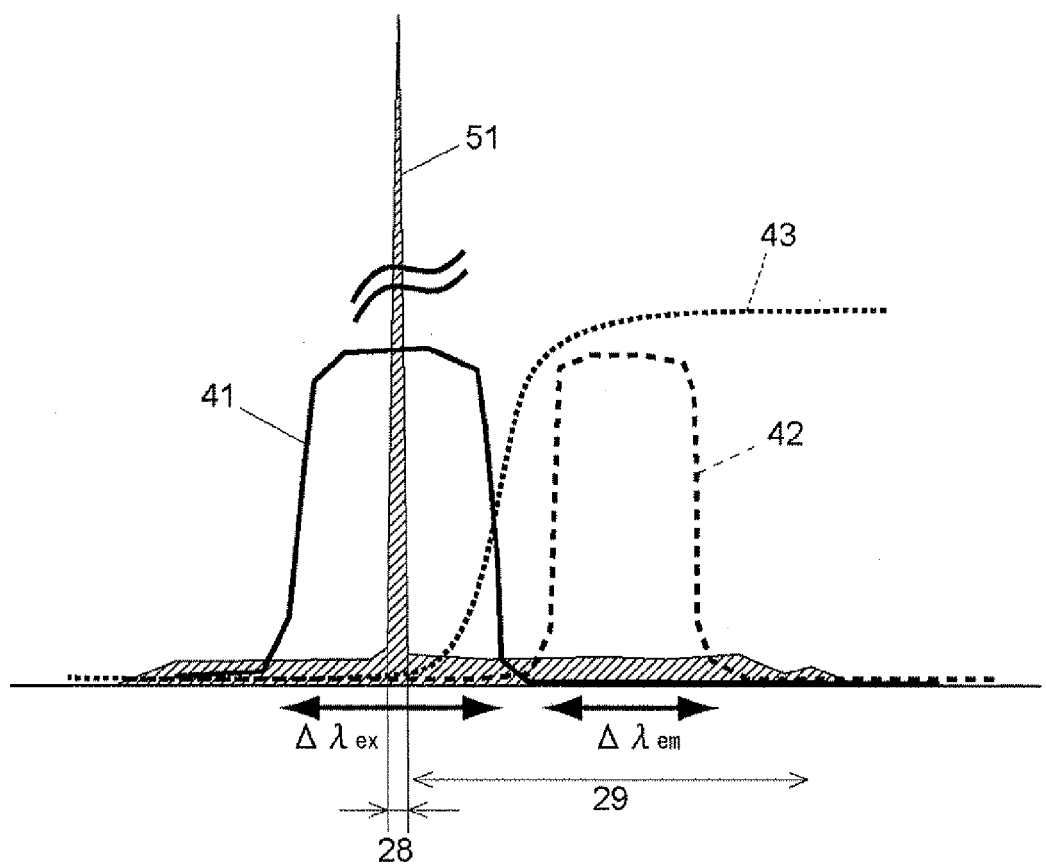
FIG. 9 The figure is a waveform chart showing the spectrum of a single-wavelength light source, and the wavelength property of each of filters.
Figure 10:
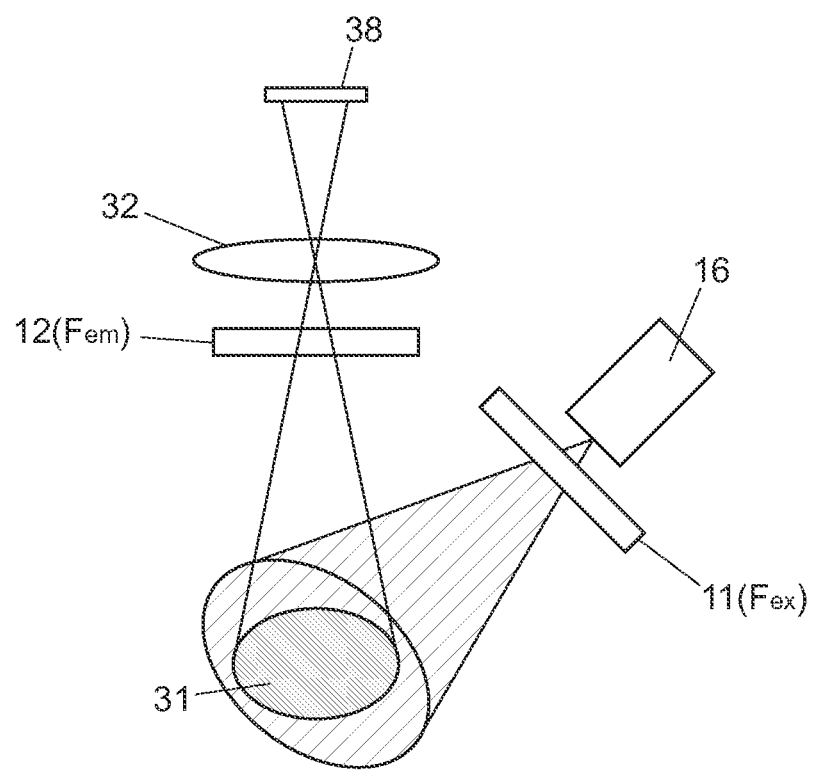
FIG. 10 The figure is a schematic structural view of a system of measuring fluorescence from a macro sample.
Figure 11:
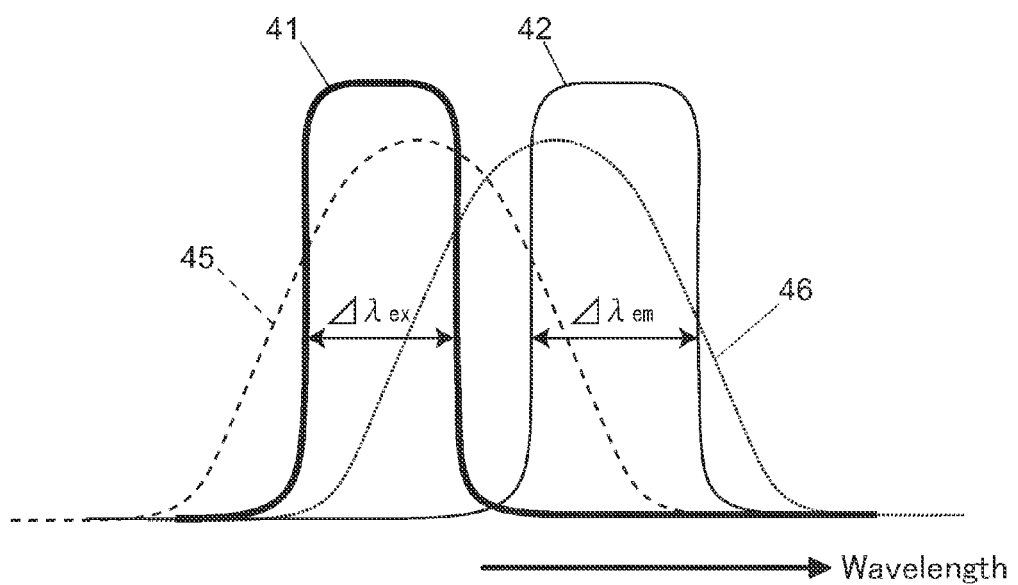
FIG. 11 The figure is a waveform chart showing the wavelength property of each of the filters relative to an excitation spectrum and a fluorescence spectrum for fluorescence measurement.

With reference to FIG. 9, a description is made about the blocked wavelength range required for the absorption filter (in the invention) as a final emphasis point. In general, any absorption filter makes use of the absorption of a substance, which is different from any multi-layered interferece filter. Thus, the (usable) wavelength is not selected at will, and the inclination from a transmission range to a blocked range is not easily made sharp. It is therefore desired that the wavelength restriction of the absorption filter (in the invention) is loose. Thus, a required restriction is considered herein. A radiated light intensity property 51 of a single-wavelength light source in FIG. 9 is in a main wavelength band 28 wherein most of light is concentrated, and in a wavelength range 29 of its tail region. The function of a transmission property 43 of the absorption filter is to cause light 51*a* from the excitation light source not to pass through the filter by effect of duplicate light-blocking of this property and a transmission property 42 of the multi-layered interferece filter.

An important point is that the duplicate light-blocking is unnecessary over the whole of the transmission range $\Delta\lambda_{ex}$ of the excitation-side filter and it is sufficient for the blocking to act only in the main wavelength range 28 from the excitation light source in the transmission range. The slope of the transmission property 43 of the absorption filter is generally gradual. In the example in FIG. 6, therefore, the transmission property 43 declines gradually from the long wavelength part (the right side in the figure) toward the left, and at a wavelength slightly longer than the main wavelength range 28 the transmittance turns into substantial zero. It is sufficient that a leak factor of, for example, $10^{-8}$ is realized only in this range. The radiation intensity in the tail region of the main wavelength band is originally weaker by f times (3 figures or more). Thus, the light-blocking in this region may not be duplicate, and is sufficient when it is attained by only the multi-layered interferece filter at the emission-side.

The present leak-light-blocking manner is again summarized herein. Regarding leak at the excitation side, which is based on an insufficiency of the emission-side filter, the blocking of the light is attained in the order of 9 figures by the properties 42 and 43. Meanwhile, regarding leak at the fluorescence detected wavelengths, which is based on an insufficiency of the excitation-side filter, the light blocking power of the multi-layered interferece filter property 41 in the order of 6 figures is combined with the f-effect that the radiation from the excitation light source is originally weak by 3 figures or more in the lateral wavelength range 51*b*, thereby attaining the light-blocking in the order of 9 figures. In short, the light-blocking in the order of 9 figures is realized by both of the excitation side and the emission-side.

Next, the main wavelength range 28 widens gradually so as to approach the transmission width $\lambda_{ex}$ of the multi-layered interferece filter 41. At this time (corresponding to a case where the light source is an LED), the radiation partially extends outside the property 43. In this case, the duplicate light-blocking does not cover the extending-out portion. Thus, the light-blocking power which is to turn into the order of 9 figures falls to 8 figures, so that the light-blocking ratio deteriorates slightly. When (the main wavelength range of) the light source further widens so that the light source turns to a continuum light. In this case, at the time when the wavelength range overlaps with the property 42, so that the property 43 does not act. Thus, only the light-blocking property of the interference filter in the order of 6 figures acts. Therefore, regarding the duplicate light-blocking manner according to this invention, the following can be mentioned: the largest advantageous effect is produced in the case of any LD, the main wavelengths of which have a narrow wavelength width $\Delta\lambda_{LS}$. The (blocking) power acts to some degree in the case of any LED although the power falls; and the light-blocking effect decreases in the case of any continuous spectrum light source.

The invention claimed is:

1. A fluorescence imaging apparatus, comprising:
an excitation light source for exciting a sample to generate fluorescence,
a two-dimensional detecting unit for detecting the fluorescence emitted from the sample,
an excitation-side filter arranged between the light source and the sample, and
an emission-side filter section arranged between the sample and the two-dimensional detecting unit to select the fluorescence emitted from the sample and lead the fluorescence to the two-dimensional detecting unit,
wherein the excitation-side filter is a filter having a transmission wavelength band which does not overlap the transmission wavelength band of the emission-side filter, and the excitation-side filter has no transmission wavelength band of the emission-side filter section,
the emission-side filter section comprises an interference filter and an absorption filter, the interference filter and the absorption filter are arranged in series in the direction along which the fluorescence travels, and the transmission wavelength bands of the interference filter and the absorption filter are combined in such a manner that the combined transmission wavelength band contains at least one part of the wavelengths of the fluorescence, and does not contain any transmission wavelength band of the excitation-side filter,
wherein the excitation light source is a single-wavelength excitation light source,
wherein the transmission wavelength band of the excitation-side filter is a band which causes light rays having main wavelengths of the single-wavelength excitation light source to be transmitted, and
wherein the absorption filter constituting the emission-side filter section has a low transmittance of 10% or less in the wavelength band of the main wavelengths of the single-wavelength excitation light source.

2. The fluorescence imaging apparatus according to claim 1, wherein the transmittance of the absorption filter is 10% or less in the transmission wavelength band of the excitation-side filter.

3. The fluorescence imaging apparatus according to claim 1, wherein the light source is a semiconductor laser which emits light having a peak wavelength of 785 nm±10 nm, and the absorption filter has a 50% transmission wavelength in the range of 800 to 860 nm.

4. The fluorescence imaging apparatus according to claim 1, wherein the light source is a semiconductor laser which emits light having a peak wavelength of 690 nm±10 nm, and the absorption filter has a 50% transmission wavelength in the range of 720 to 780 nm.

5. The fluorescence imaging apparatus according to claim 1, wherein the light source is a semiconductor laser which emits light having a peak wavelength of 658 nm±10 nm, and the absorption filter has a 50% transmission wavelength in the range of 690 to 740 nm.

6. The fluorescence imaging apparatus according to claim 1, wherein the light source is a semiconductor laser which emits light having a peak wavelength of 808 nm±10 nm, and the absorption filter has a 50% transmission wavelength in the range of 820 to 870 nm.

7. A fluorescent image detecting method for detecting a fluorescent image, using a fluorescence imaging apparatus comprising an excitation light source for exciting a sample to generate fluorescence, a two-dimensional detecting unit for detecting the fluorescence emitted from the sample, an excitation-side filter arranged between the light source and the sample, and an emission-side filter section arranged between the sample and the two-dimensional detecting unit to select the fluorescence emitted from the sample and lead the fluorescence to the two-dimensional detecting unit,
wherein as the excitation-side filter, use is made of a filter having a transmission wavelength band which does not overlap the transmission wavelength band of the emission-side filter section, the excitation-side filter having no transmission wavelength band of the emission-side filter section, and
as the emission-side filter section, use is made of a section wherein an interference filter and an absorption filter are arranged in series in the direction along which the fluorescence travels, and the transmission wavelength bands of the interference filter and the absorption filter are combined in such a manner that the combined transmission wavelength band contains at least one part of the wavelengths of the fluorescence, and does not contain any transmission wavelength band of the excitation-side filter,
wherein as the excitation light source, a single-wavelength excitation light source is used,
wherein as the excitation-side filter, use is made of a filter having a transmission wavelength band which causes light rays having main wavelengths of the single-wavelength excitation light source to be transmitted, and
wherein as the absorption filter of the emission-side filter section, use is made of a filter having a transmittance of 10% or less in the wavelength band of the main wavelengths of the single-wavelength excitation light source.

8. The fluorescent image detecting method according to claim 7, wherein the excitation light source is a semiconductor laser which emits light having a peak wavelength of 785 nm±10 nm, and the absorption filter has a 50% transmission wavelength in the range of 800 to 860 nm.

9. The fluorescent image detecting method according to claim 7, wherein the excitation light source is a semiconductor laser which emits light having a peak wavelength of 690 nm±10 nm, and the absorption filter has a 50% transmission wavelength in the range of 720 to 780 nm.

10. The fluorescent image detecting method according to claim 7 wherein the excitation light source is a semiconductor laser Which emits light having a peak wavelength of 658 nm±10 nm, and the absorption filter has a 50% transmission wavelength in the range of 690 to 740 nm.

11. The fluorescent image detecting method according to claim 7, wherein the excitation light source is a semiconductor laser which emits light having a peak wavelength of 808 nm±10 nm, and the absorption filter has a 50% transmission wavelength in the range of 820 to 870 nm.

12. The fluorescent image detecting method according to claim 7, wherein the sample contains indocyanine green as a fluorescent dye.

\* \* \* \* \*